(12) United States Patent
Niino et al.

(10) Patent No.: US 12,130,460 B2
(45) Date of Patent: Oct. 29, 2024

(54) OPTICAL CONNECTOR

(71) Applicant: KYOCERA Corporation, Kyoto (JP)

(72) Inventors: Noritaka Niino, Soraku-gun (JP); Eri Takeuchi, Yokohama (JP); Tomoyoshi Akashi, Nara (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 18/033,952

(22) PCT Filed: Oct. 29, 2021

(86) PCT No.: PCT/JP2021/040043
§ 371 (c)(1),
(2) Date: Apr. 26, 2023

(87) PCT Pub. No.: WO2022/092270
PCT Pub. Date: May 5, 2022

(65) Prior Publication Data
US 2023/0393321 A1    Dec. 7, 2023

(30) Foreign Application Priority Data

Oct. 30, 2020  (JP) ................................ 2020-182979
Jan. 29, 2021  (JP) ................................ 2021-012917
Jan. 29, 2021  (JP) ................................ 2021-012918

(51) Int. Cl.
*F21V 8/00*    (2006.01)
*F21V 9/32*    (2018.01)

(52) U.S. Cl.
CPC .............. *G02B 6/0008* (2013.01); *F21V 9/32* (2018.02); *G02B 6/0006* (2013.01)

(58) Field of Classification Search
CPC ............... A61B 1/2736; F21V 7/22–30; F21V 9/30–45; F21V 29/502–503; G02B 6/005–001
See application file for complete search history.

(56) References Cited

U.S. PATENT DOCUMENTS 9,291,759 B2 *  3/2016  Toyota ................. G02B 6/0008
9,863,595 B2 *  1/2018  Takahira ............... F21S 41/337
(Continued)

FOREIGN PATENT DOCUMENTS

JP    2012-015001 A    1/2012
JP    2012-099283 A    5/2012
(Continued)

*Primary Examiner* — Jason M Han
(74) *Attorney, Agent, or Firm* — Volpe Koenig

(57) ABSTRACT

A wavelength converter emits light in response to laser light emitted from a light emitter. The wavelength converter includes a surface including a first area to directly receive the laser light from the light emitter, and a second area located on a member. The light emitted from the wavelength converter includes a first component emitted directly from the wavelength converter and input directly into the light receiver, and a second component emitted from the second area, reflected from the member, and input into the light receiver. The member includes a surface including a third area to receive the second component. The third area has a reflectance for the light greater than a reflectance of the wavelength converter for the light in the second area.

7 Claims, 26 Drawing Sheets

(56) References Cited

U.S. PATENT DOCUMENTS

| | | | |
|---|---|---|---|
| 2012/0104934 A1 | 5/2012 | Fukai et al. |
| 2013/0314937 A1 | 11/2013 | Takahashi et al. |
| 2015/0062943 A1 | 3/2015 | Takahira et al. |
| 2018/0317757 A1 | 11/2018 | Hayashi |
| 2020/0232610 A1 | 7/2020 | Raring et al. |

FOREIGN PATENT DOCUMENTS

| | | |
|---|---|---|
| JP | 2013-246943 A | 12/2013 |
| JP | 2015-088283 A | 5/2015 |
| WO | 2019/163741 A1 | 8/2019 |

\* cited by examiner

OPTICAL CONNECTOR

CROSS-REFERENCE TO RELATED APPLICATIONS

This application claims priority to Japanese Patent Application Nos. 2020-182979 filed on Oct. 30, 2020, 2021-12917 filed on Jan. 29, 2021, and 2021-12918 filed on Jan. 29, 2021, the entire disclosure of which is incorporated by reference.

TECHNICAL FIELD

The present disclosure relates to an optical connector.

BACKGROUND OF INVENTION

Patent Literature 1 describes a wavelength converter that emits light in response to laser light.

CITATION LIST

Patent Literature

Patent Literature 1: Japanese Unexamined Patent Application Publication No. 2012-15001

SUMMARY

One or more aspects of the disclosure are directed to an optical connector and an illumination system. In one embodiment, the optical connector includes a light emitter, a wavelength converter, a light receiver, and a member. The light emitter emits laser light. The wavelength converter receives the laser light and emits light with a wavelength spectrum different from a wavelength spectrum of the laser light in response to the laser light. The light receiver receives input of the light from the wavelength converter. The member reflects the light from the wavelength converter. The wavelength converter includes a surface including a first area to directly receive the laser light from the light emitter, and a second area located on the member. The light emitted from the wavelength converter includes a first component emitted directly from the wavelength converter and input directly into the light receiver, and a second component emitted from the second area, reflected from the member, and input into the light receiver. The member includes a surface including a third area to receive the second component. The member has a reflectance for the light in the third area greater than a reflectance of the wavelength converter for the light in the second area.

In one embodiment, an illumination system includes the optical connector described above to radiate, as illumination light, the light emitted from the wavelength converter in the optical connector.

DESCRIPTION OF EMBODIMENTS

Figure 1:
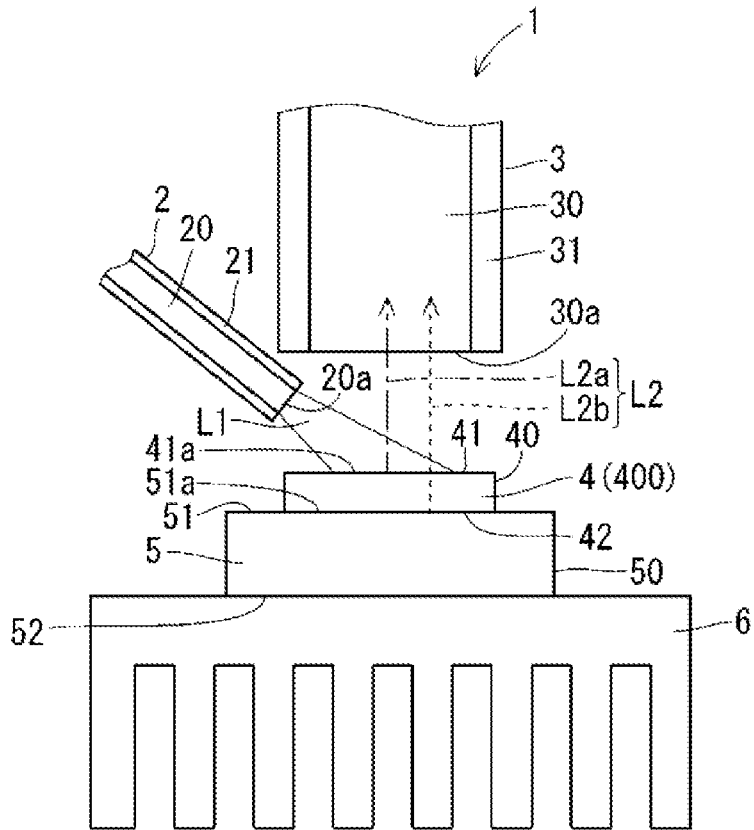
FIG. 1 is a schematic diagram of an example optical connector.

FIG. 1 is a schematic diagram of an example optical connector 1. As illustrated in FIG. 1, the optical connector 1 includes, for example, a light emitter 2, a light receiver 3, a wavelength converter 4, a substrate 5, and a heat dissipater 6. In the optical connector 1, laser light L1 emitted from the light emitter 2 is applied to the wavelength converter 4, and light L2 emitted from the wavelength converter 4 in response to the laser light L1 is input into the light receiver 3. Each of the light emitter 2 and the light receiver 3 is, for example, an optical fiber. The light emitter 2 that is an optical fiber may be hereafter referred to as an optical fiber 2. The light receiver 3 that is an optical fiber may be hereafter referred to as an optical fiber 3. FIG. 1 illustrates the optical fibers 2 and 3 in a cross section taken along their optical axes.

The laser light L1 is input into the optical fiber 2 (also referred to as a first optical fiber), which transmits the input laser light L1. The laser light L1 travels directly from the optical fiber 2 to the wavelength converter 4. The optical fiber 2 includes, for example, a core 20 that transmits the laser light L1 and a cladding 21 surrounding the core 20. The optical fiber 2 may be, for example, a quartz fiber made of quartz glass, a plastic fiber made of plastic, or an optical fiber made of another material. The optical fiber 2 may be a single mode optical fiber, or may be a multi-mode optical fiber.

The core 20 includes an output surface 20a through which the laser light L1 is output. The output surface 20a of the core 20 may also be referred to as an output end face 20a. The output surface 20a is, for example, circular. The output surface 20a is located near the wavelength converter 4. The output surface 20a faces toward the wavelength converter 4. The laser light L1 output through the output surface 20a travels directly to the wavelength converter 4. The optical fiber 2 may include a member that surrounds the cladding 21. The member surrounding the cladding 21 may include a single layer or multiple layers. The member surrounding the cladding 21 may include a protective layer.

The laser light L1 may be, for example, short-wavelength laser light with a wavelength not greater than 460 nm. The laser light L1 may be, for example, short-wavelength laser light with a wavelength not greater than 440 nm. The laser light L1 may be, for example, violet laser light with a wavelength of 405 nm.

The wavelength converter 4 can emit the light L2 with a wavelength spectrum different from the wavelength spectrum of the laser light L1 in response to the laser light L1 received from the optical fiber 2. The light L2 is, for example, visible light. The wavelength converter 4 is, for example, a flat plate. The wavelength converter 4 includes a surface 40 including a first main surface 41 (also referred to as a first surface 41) and a second main surface 42 (also referred to as a second surface 42) that are flat and face each other. The surface 40 of the wavelength converter 4 includes a first area 41a (also referred to as an illumination area 41a) that receives the laser light L1. In the example of FIG. 1, the laser light L1 is applied to, for example, the first main surface 41 that may include the illumination area 41a. The illumination area 41a can be calculated by, for example, obtaining images with a measurement device based on light emission and reception or with another device. A member that reflects light L2 is located on the second main surface 42 (also referred to as a second area 42). The member that reflects the light L2 on the second main surface 42 may be hereafter referred to as a high-reflectance member. The light L2 may be referred to as conversion light L2. In this example, the substrate 5 is a high-reflectance member.

The wavelength converter 4 may be, for example, a phosphor portion 400 containing phosphors. The phosphors contained in the phosphor portion 400 can emit fluorescence in response to the laser light L1. The peak wavelength of the wavelength spectrum of the fluorescence emitted from the phosphors (also referred to as the peak wavelength) may be greater or less than the peak wavelength of the wavelength spectrum of the laser light L1.

The phosphor portion 400 contains, for example, numerous phosphors. The numerous phosphors include, for example, one or more types of phosphors. The phosphor portion 400 may contain multiple types of phosphors with different peak wavelengths. In this case, the phosphor portion 400 may contain, for example, a phosphor that emits red (R) fluorescence in response to the laser light L1 (also referred to as a red phosphor), a phosphor that emits green (G) fluorescence in response to the laser light L1 (also referred to as a green phosphor), and a phosphor that emits blue (B) fluorescence in response to the laser light L1 (also referred to as a blue phosphor). The red phosphor is, for example, a phosphor with a peak wavelength of the wavelength spectrum of fluorescence in a range of about 620 to 750 nm emitted in response to the laser light L1. The green phosphor is, for example, a phosphor with a peak wavelength of the wavelength spectrum of fluorescence in a range of about 495 to 570 nm emitted in response to the laser light L1. The blue phosphor is, for example, a phosphor with a peak wavelength of the wavelength spectrum of fluorescence in a range of about 450 to 495 nm emitted in response to the laser light L1.

When the phosphor portion 400 contains multiple types of phosphors, the conversion light L2 emitted from the phosphor portion 400 includes fluorescence emitted from the multiple types of phosphors. In other words, the conversion light L2 includes multiple color components. When the phosphor portion 400 contains red, green, and blue phosphors, the conversion light L2 includes fluorescence emitted from the red, green, and blue phosphors.

When the phosphor portion 400 contains multiple types of phosphors, the wavelength spectrum of the conversion light L2 has multiple wavelength peaks different from one another. In the phosphor portion 400 containing three or more types of phosphors, for example, the wavelength spectrum of the conversion light L2 has three or more wavelength peaks different from one another. In the phosphor portion 400 containing red, green, and blue phosphors, the wavelength spectrum of the conversion light L2 has the peak of the wavelength of the fluorescence emitted from the red phosphor, the peak of the wavelength of the fluorescence emitted from the green phosphor, and the peak of the wavelength of the fluorescence emitted from the blue phosphor. The conversion light L2 may be pseudo white light or visible light with another color temperature.

The phosphor portion 400 may contain a phosphor other than a red, green or, blue phosphor. The phosphor portion 400 may contain, for example, a phosphor that emits blue-green fluorescence in response to the laser light L1 (also referred to as a blue-green phosphor). The phosphor portion 400 may contain a phosphor that emits yellow fluorescence in response to the laser light L1 (also referred to as a yellow phosphor). The phosphor portion 400 may contain at least one of a red, green, blue, blue-green, or yellow phosphor.

The blue-green phosphor is, for example, a phosphor with a peak wavelength of fluorescence emitted in response to the laser light L1 being about 495 nm. The yellow phosphor is, for example, a phosphor with a peak wavelength of fluorescence emitted in response to the laser light L1 in a range of about 570 to 590 nm.

The phosphor portion 400 may be, for example, low-melting glass containing numerous phosphors. In some embodiments, the phosphor portion 400 may be crystallized glass with a low melting point containing numerous phosphors. In some embodiments, the phosphor portion 400 may be a ceramic material containing numerous phosphors. In some embodiments, the phosphor portion 400 may be a fluorescent ceramic bulk. In this case, the phosphor portion 400 is made of a phosphor material alone.

The substrate 5 supports the wavelength converter 4 (or the phosphor portion 400). The substrate 5 is bonded to the second main surface 42 of the wavelength converter 4. The substrate 5 includes the surface 50 including a first main surface 51 (also referred to as an upper surface 51) and a second main surface 52 (also referred to as a lower surface 52) that are flat and opposite to each other. The wavelength converter 4 is bonded to the first main surface 51 of the substrate 5.

The substrate 5 that is a high-reflectance member can reflect the conversion light L2 emitted from the wavelength converter 4. The substrate 5 can also reflect, for example, the laser light L1. The substrate 5 functions as a member that reflects the conversion light L2 and the laser light L1.

The substrate 5 is made of, for example, a metal. The substrate 5 may be made of, for example, an aluminum alloy containing aluminum as a main component, aluminum, or another material.

The wavelength converter 4 may be bonded directly to the substrate 5, or may be bonded with a bonding material. For example, a wavelength converter 4 that is low-melting glass containing numerous phosphors may be bonded directly to the substrate 5 by oxygen bonding. In other words, the wavelength converter 4 may be bonded directly to the substrate 5 by oxidative coupling, in which oxygen in an oxide film on the first main surface 51 of the substrate 5 combines, by heating, with oxygen in the low-melting glass (or oxide glass) of the wavelength converter 4. The wavelength converter 4 may be bonded directly to the substrate 5 with, for example, minute recesses and protrusions of a few micrometers on the first main surface 51 of the substrate 5 that anchor the wavelength converter 4. In other words, the wavelength converter 4 may be bonded directly to the substrate 5 with the low-melting glass in fluid, which is the material of the wavelength converter 4. The low-melting glass hardens after fitting with the protrusions and recesses on the first main surface 51 of the substrate 5. The wavelength converter 4 may be bonded to the substrate 5 using, for example, a bonding material made of a transparent resin transmissive to laser light L1 and the conversion light L2.

The conversion light L2 includes a first component L2a emitted directly from the wavelength converter 4 and input directly into the optical fiber 3. More specifically, the conversion light L2 includes, for example, the first component L2a emitted directly from the illumination area 41a of the wavelength converter 4 and input directly into the optical fiber 3. In other words, the first component L2a is a component of the conversion light L2 emitted from the first area 41a and input into the optical fiber 3 without being reflected from the substrate 5. The conversion light L2 further includes a second component L2b emitted from the second area 42 of the wavelength converter 4, reflected from the substrate 5, and then input into the optical fiber 3. The second component L2b is reflected from the first main surface 51 of the substrate 5, transmitted through the wavelength converter 4, and input into the optical fiber 3. The first main surface 51 of the substrate 5 includes a third area 51a (also referred to as an illumination area 51a) that receives the second component L2b. The conversion light L2 also includes a component that is not input into the optical fiber 3, in addition to the first component L2a and the second component L2b. The conversion light L2 may include a component that is input into the optical fiber 3 other than the first component L2a or the second component L2b.

In this example, a surface 50 of the substrate 5 has a greater reflectance for the conversion light L2 than on the surface 40 of the wavelength converter 4 for the conversion light L2. The surface 50 includes the illumination area 51a, and the surface 40 includes the second area 42. The reflectance for the conversion light L2 in the illumination area 51a is thus greater than the reflectance for the conversion light L2 in the second area 42 of the wavelength converter 4. The reflectance of the surface 40 of the wavelength converter 4 for the conversion light L2 is, for example, several percent. The reflectance of the surface 50 of the substrate 5 for the conversion light L2 is, for example, not less than 35%. The reflectance of the surface 50 of the substrate 5 for the conversion light L2 is not limited to this, but may be, for example, not less than 40, 50, 60, 70, or 80%. The reflectance of an object for light also depends on the wavelength of the light. The reflectance varies as the wavelength of the light varies. The reflectance can be determined based on the material of the object, or by measurement with, for example, a spectrophotometer.

In this example, the reflectance of the surface 50 of the substrate 5 for the laser light L1 is greater than the reflectance of the surface 40 of the wavelength converter 4 for the laser light L1. The surface 50 includes the illumination area 51a, and the surface 40 includes the second area 42. The reflectance for the laser light L1 in the illumination area 51a is thus greater than the reflectance for the laser light L1 in the second area 42 of the wavelength converter 4. The reflectance of the surface 40 of the wavelength converter 4 for the laser light L1 is, for example, several percent. The reflectance of the surface 50 of the substrate 5 for the laser light L1 is, for example, not less than 35%. The reflectance of the surface 50 of the substrate 5 for the laser light L1 is not limited to this, but may be, for example, not less than 40, 50, 60, 70, or 80%.

The reflectance of the surface 50 of the substrate 5 for the conversion light L2 may be less than or equal to the reflectance of the surface 40 of the wavelength converter 4 for the conversion light L2. The reflectance of the surface 50 of the substrate 5 for the laser light L1 may be less than or equal to the reflectance of the surface 40 of the wavelength converter 4 for the laser light L1.

The laser light L1 output from the optical fiber 2 includes a transmission component that is to be transmitted through the wavelength converter 4 and to reach the third area 51a of the substrate 5 (or the illumination area 51a). The transmission component is reflected from the third area 51a of the substrate 5 back to the wavelength converter 4. The wavelength converter 4 then emits light in response to the transmission component. This light may be referred to as light responsive to the transmission component. A portion of the light responsive to the transmission component is output through the first area 41a as part of the first component L2a and is input directly into the optical fiber 3. A portion of the light responsive to the transmission component is output through the second area 42 as part of the second component L2b and is input into the optical fiber 3 after being reflected from the substrate 5.

The optical fiber 3 (also referred to as a second optical fiber) transmits the input conversion light L2. The optical fiber 3 includes, for example, a core 30 and a cladding 31 surrounding the core 30. The conversion light L2 is input into the core 30, which transmits the input conversion light L2. The optical fiber 3 may be, for example, a quartz fiber made of quartz glass, a plastic fiber made of plastic, or an optical fiber made of another material. The optical fiber 3 may be a single mode optical fiber, or may be a multi-mode optical fiber.

The core 30 includes an input surface 30*a* through which the conversion light L2 is input. The input surface 30*a* of the core 30 may also be referred to as an input end face 30*a*. The input surface 30*a* is, for example, circular. The input surface 30*a* is located near the illumination area 41*a* of the wavelength converter 4. The input surface 30*a* faces toward the wavelength converter 4. More specifically, the input surface 30*a* faces toward the illumination area 41*a* of the wavelength converter 4. The input surface 30*a* is, for example, located perpendicularly above the illumination area 41*a* of the wavelength converter 4. The first component L2*a* and the second component L2*b* of the conversion light L2 are incident on the input surface 30*a*. The optical fiber 3 may include a member that surrounds the cladding 31. The member surrounding the cladding 31 may include a single layer or multiple layers. The member surrounding the cladding 31 may include a protective layer.

The optical fibers 2 and 3 are located on the same side of the wavelength converter 4. The optical fibers 2 and 3 are located to face the first main surface 41 of the wavelength converter 4. The substrate 5 is located opposite to the optical fibers 2 and 3 from the wavelength converter 4. The substrate 5 is located adjacent to the second main surface 42 of the wavelength converter 4.

The input surface 30*a* of the core 30 in the optical fiber 3, or in other words, the input surface 30*a* included in the light receiver 3 that receives the conversion light L2 is parallel to, for example, the first area 41*a* of the wavelength converter 4. The input surface 30*a* faces the first area 41*a*. The optical axis of the optical fiber 3 extends in a direction perpendicular to the first area 41*a*. In one or more embodiments of the present disclosure, being parallel refers to being at a substantially parallel position that may slightly deviate from parallelism by error with, for example, a tilt of several degrees from the parallel position.

The output surface 20*a* of the core 20 in the optical fiber 2, or in other words, the output surface 20*a* included in the light emitter 2 and through which the laser light L1 is output is, for example, tilted from a direction parallel to the first area 41*a* of the wavelength converter 4. In other words, the output surface 20*a* is tilted from a direction perpendicular to the first area 41*a*. The optical axis of the optical fiber 2 is tilted from a direction perpendicular to the first area 41*a*. The laser light L1 is obliquely incident on the first area 41*a*.

The optical fiber 2 and the optical fiber 3 are located not to cross each other. The output surface 20*a* of the optical fiber 2, for example, does not overlap the input surface 30*a* of the optical fiber 3 in the direction perpendicular to the first area 41*a*. The output surface 20*a* is, for example, closer to the first area 41*a* than the input surface 30*a* in the direction perpendicular to the first area 41*a*. The input surface 30*a* may be closer to the first area 41*a* than the output surface 20*a* in the direction perpendicular to the first area 41*a*. The input surface 30*a* and the output surface 20*a* may be aligned in a direction parallel to the first area 41*a*.

The heat dissipater 6 can dissipate heat generated by the wavelength converter 4. The heat dissipater 6 is, for example, a member that uses no power supply. The heat dissipater 6 is, for example, a metal heat sink with heat-dissipating fins. The heat dissipater 6 may be, for example, made of an aluminum alloy containing aluminum as a main component, aluminum, or another material. The heat dissipater 6 may be made of the same material as or a different material from the substrate 5. The heat dissipater 6 has, for example, a higher thermal conductivity than the wavelength converter 4. The substrate 5 has, for example, a higher thermal conductivity than the wavelength converter 4. In addition to the heat dissipater 6, the substrate 5 may dissipate heat generated by the wavelength converter 4. The heat dissipater 6 may have a thermal conductivity higher than, lower than, or equal to the substrate 5. Thermal conductivity can be measured with, for example, a steady-state method or a non-steady state method. The non-steady state method includes the laser flash method, the guarded heat flowmeter method in accordance with ASTM E1530, the hot wire (probe) method in accordance with JIS R 2616 or ASTM D5930, and the temperature modulation method in accordance with ISO 22007-6.

The substrate 5 is fixed to the heat dissipater 6. The heat generated by the wavelength converter 4 is transferred to the heat dissipater 6 through the substrate 5, and is dissipated from the heat dissipater 6 into space. The substrate 5 may be fixed to the heat dissipater 6 with various methods. For example, the substrate 5 may be screwed to the heat dissipater 6 with heat-dissipating grease placed between the substrate 5 and the heat dissipater 6. In another example, the substrate 5 may be fixed to the heat dissipater 6 with an adhesive containing a high thermal conductivity filler. In another example, the substrate 5 may be fixed to the heat dissipater 6 with a sintering paste.

The heat dissipater 6 may be a member with a different structure that uses no power supply. The heat dissipater 6 may be, for example, a heat pipe that is a type of heat sink. In a heat pipe, for example, a working fluid evaporates in a heating section into vapor, which flows at high speed to a low-temperature section of the heat pipe and condenses in the low-temperature section. The working fluid condenses back into a liquid, and then returns, by capillary action, to the heating section. The heat pipe dissipates heat through such consecutive phase changes. The heat dissipater 6 may also be a member that uses a power supply. The heat dissipater 6 may be, for example, a Peltier device or a fan.

In the above example, the light emitter 2 is an optical fiber, but may be another member. The light emitter 2 may be, for example, a rod lens. The light emitter 2 may also be, for example, an integrator lens, a hollow mirror, or a light guide. The light receiver 3 may be, for example, a rod lens. The light receiver 3 may also be, for example, an integrator lens, a hollow mirror, or a light guide. The light emitter 2 and the light receiver 3 may be members of the same type or different types. Each of the light emitter 2 and the light receiver 3 may be, for example, a rod lens. The light emitter 2 may be an optical fiber, and the light receiver 3 may be a rod lens. The light emitter 2 may be a rod lens, and the light receiver 3 may be an optical fiber. A rod lens herein is a glass or transparent resin member that is an optical element transmitting light through reflection of light from its side surface. The side surface of the rod lens may have a metal film, such as an aluminum film, to enhance the rod lens characteristics. The rod lens may also have a refractive index distribution profile in the direction of the rod lens diameter to function as a lens.

As described above, in the optical connector 1 in this example, the laser light L1 travels from the light emitter 2 directly to the wavelength converter 4. This eliminates, for example, an optical system including, for example, an optical mirror (also referred to as an optical system for laser application) to direct the laser light L1 to the wavelength converter 4. Unlike in this example, an optical connector 1 including an optical system for laser application involves adjusting the positions of each component of the optical system for laser application in assembling the optical connector 1. This may complicate the assembly process of the optical connector 1. The optical connector 1 in this example eliminates an optical system for laser application and thus simplifies the assembly process of the optical connector 1. This further simplifies the structure of the optical connector 1.

In the optical connector 1 in this example, the conversion light L2 emitted from the wavelength converter 4 directly travels to the light receiver 3. This eliminates, for example, an optical system including, for example, an optical mirror (also referred to as an optical system for input) to direct the conversion light L2 to the light receiver 3. Unlike in this example, an optical connector 1 including an optical system for input involves adjusting the positions of each component of the optical system for input in assembling the optical connector 1. This may complicate the assembly process of the optical connector 1. The optical connector 1 in this example eliminates an optical system for input and thus simplifies the assembly process of the optical connector 1. This further simplifies the structure of the optical connector 1.

The optical connector 1 may include an optical system to redirect the component of the laser light L1 that is reflected from the surface 40 of the wavelength converter 4 back to the wavelength converter 4. The optical connector 1 may include an optical system to collect the component of the conversion light L2 that is not input into the light receiver 3 and direct the component to the light receiver 3.

In the optical connector 1 in this example, the substrate 5 being a high-reflectance member has a greater reflectance for the conversion light L2 in the illumination area 51a than on the surface 40 of the wavelength converter 4. This increases the intensity of the second component L2b of the conversion light L2 emitted from the second area 42 of the wavelength converter 4, reflected from the illumination area 51a of the substrate 5, and the input into the light receiver 3. This allows the conversion light L2 emitted from the wavelength converter 4 to be efficiently input into the light receiver 3. Thus, the optical connector 1 has a less connection loss.

In this example, the substrate 5 has a greater reflectance for the laser light L1 in the illumination area 51a than on the surface 40 of the wavelength converter 4. This increases the intensity of the transmission component of the laser light L1 transmitted through the wavelength converter 4 and reflected from the illumination area 51a of the substrate 5. Thus, the intensity of the light responsive to the transmission component emitted from the wavelength converter 4 increases. This improves the efficiency of light emission from the wavelength converter 4.

The optical connector 1 in this example including the heat dissipater 6 to dissipate heat generated by the wavelength converter 4 further reduces deterioration of the performance of the wavelength converter 4 under heating.

In this example, both the light emitter 2 and the light receiver 3 located to face the illumination area 41a of the wavelength converter 4, as illustrated in FIG. 1 for example, also allow the heat dissipater 6 to be in a space opposite to the illumination area 41a from the wavelength converter 4 (facing the second area 42). This facilitates heat dissipation from the wavelength converter 4.

In this example, the position of the input surface 30a of the light receiver 3, being parallel to the illumination area 41a of the wavelength converter 4, can also be adjusted easily. For example, simply moving the light receiver 3 along its optical axis can position the input surface of the light receiver 3 with respect to the illumination area 41a of the wavelength converter 4.

For the output surface 20a of the light emitter 2 tilted from a direction parallel to the illumination area 41a of the wavelength converter 4, as in this example, adjusting the position of the output surface 20a of the light emitter 2 may be complicated. Positioning of the output surface with respect to the illumination area 41a may involve, for example, in addition to moving the light emitter 2 along its optical axis, changing the direction of the output surface 20a, moving the light emitter 2 in a direction parallel to the illumination area 41a, or moving the light emitter 2 in a direction perpendicular to the illumination area 41a.

For the output surface 20a tilted from a direction parallel to the illumination area 41a, the conversion light L2 emitted from the wavelength converter 4 is efficiently input into the light receiver 3. This will be described below.

Figure 2:
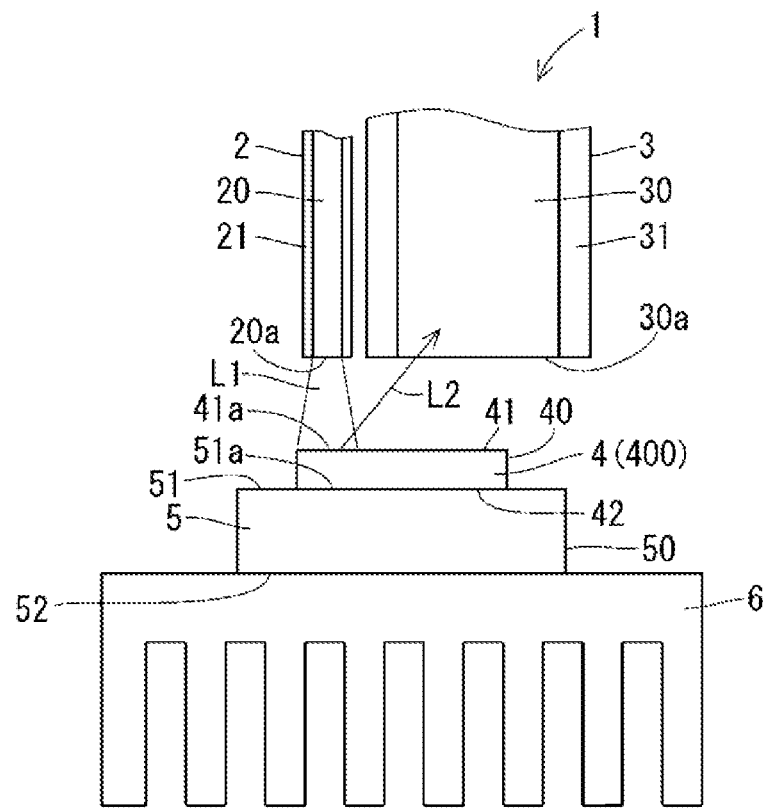
FIG. 2 is a schematic diagram of an example optical connector.

In the example illustrated in FIG. 2, the output surface 20a is parallel to the illumination area 41a. The intensity of the conversion light L2 has a peak, for example, in a direction substantially perpendicular to the area of the wavelength converter 4 that receives the laser light L1, or more specifically, the illumination area 41a. In the example of FIG. 2, the light emitter 2 located substantially perpendicularly above the illumination area 41a causes the conversion light L2 to be input less efficiently into the input surface 30a of the light receiver 3.

In contrast, tilting the output surface 20a of the light emitter 2 from a direction parallel to the illumination area 41a of the wavelength converter 4, as illustrated in FIG. 1, allows the input surface 30a of the light receiver 3 to be substantially perpendicularly above the illumination area 41a of the wavelength converter 4. This thus allows the conversion light L2 emitted from the wavelength converter 4 to be efficiently input into the light receiver 3.

Figure 3:
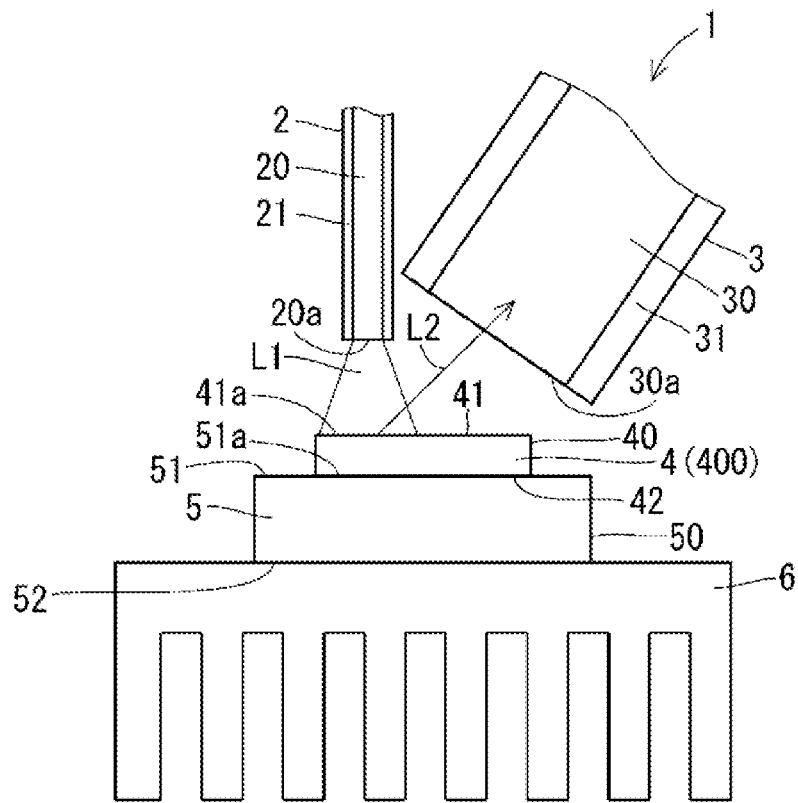
FIG. 3 is a schematic diagram of an example optical connector.

In the optical connector 1, as illustrated in FIG. 2, the illumination area 41a may be parallel to both of the output surface 20a of the light emitter 2 and the input surface 30a of the light receiver 3, or as illustrated in FIG. 3, the illumination area 41a may be parallel to the output surface but not parallel to the input surface 30a. For the output surface 20a of the optical fiber 2 parallel to the illumination area 41a, as in the examples in FIGS. 2 and 3, the position of the output surface of the light emitter 2 can be adjusted easily as in the structure with the input surface 30a of the light receiver 3 being parallel to the illumination area 41a.

Figure 4:
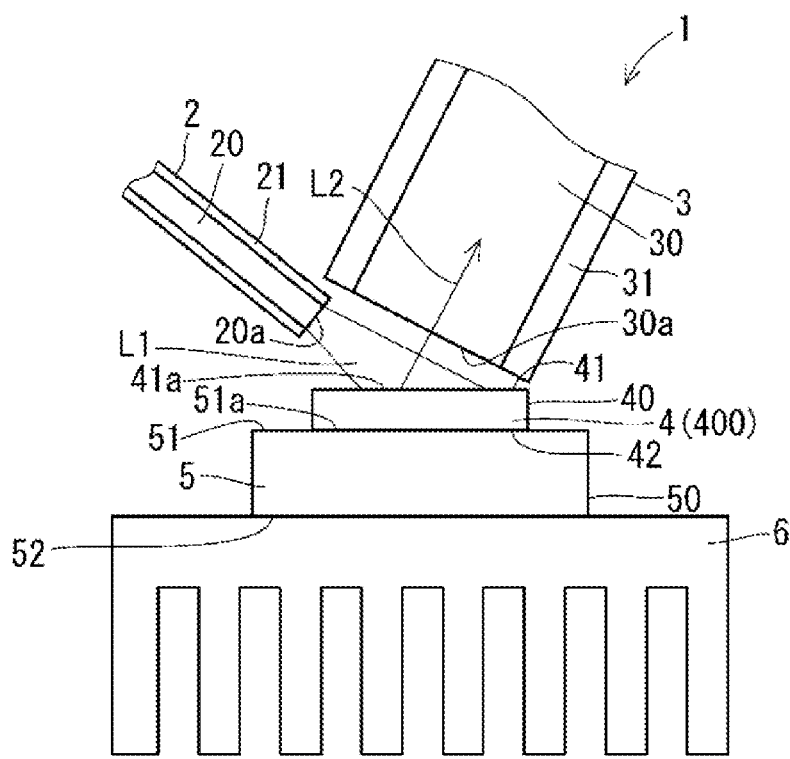
FIG. 4 is a schematic diagram of an example optical connector.

In the optical connector 1, as illustrated in FIG. 4, the output surface 20a of the light emitter 2 and the input surface 30a of the light receiver 3 may be tilted from a direction parallel to the illumination area 41a in directions different from each other.

In the example of FIG. 4, the input surface 30a is located in the direction of regular reflection of the laser light L1 incident on the illumination area 41a, or more specifically, in the direction of regular reflection of the component of the laser light L1 that travels along its center line (also referred to as the central component). The light emitter 2 and the light receiver 3 are located to cause the input surface 30a to be, for example, perpendicular or substantially perpendicular to the direction of regular reflection of the central component of the laser light L1 incident on the illumination area 41a. The light emitter 2 and the light receiver 3 are located not to cross each other and to cause the output surface 20a and the input surface 30a to be tilted from a direction parallel to the illumination area 41a in directions different from each other. In the example of FIG. 4, the output surface 20a and the input surface 30a are tilted from a direction parallel to the illumination area 41a in directions different from each other to cause the input surface 30a to face toward the illumination area 41a.

As described above, the intensity of the conversion light L2 has a peak in a direction substantially perpendicular to the illumination area 41a. However, when the output surface 20a of the light emitter 2 is tilted as in the example of FIG. 4, the intensity of the conversion light L2 has a peak in a direction slightly shifted in the direction of regular reflection from the direction perpendicular to the illumination area 41a. Thus, tilting the input surface 30a of the light receiver 3 as illustrated in FIG. 4 allows the conversion light L2 emitted from the wavelength converter 4 to be efficiently input into the optical fiber 3.

Figure 5:
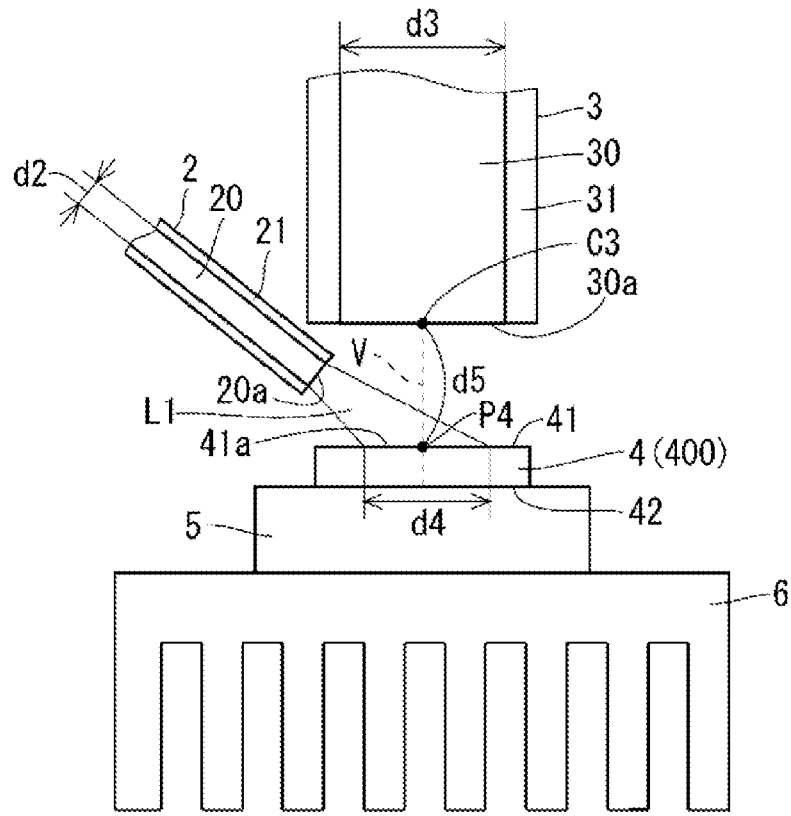
FIG. 5 is a schematic diagram of an example optical connector.
Figure 6:
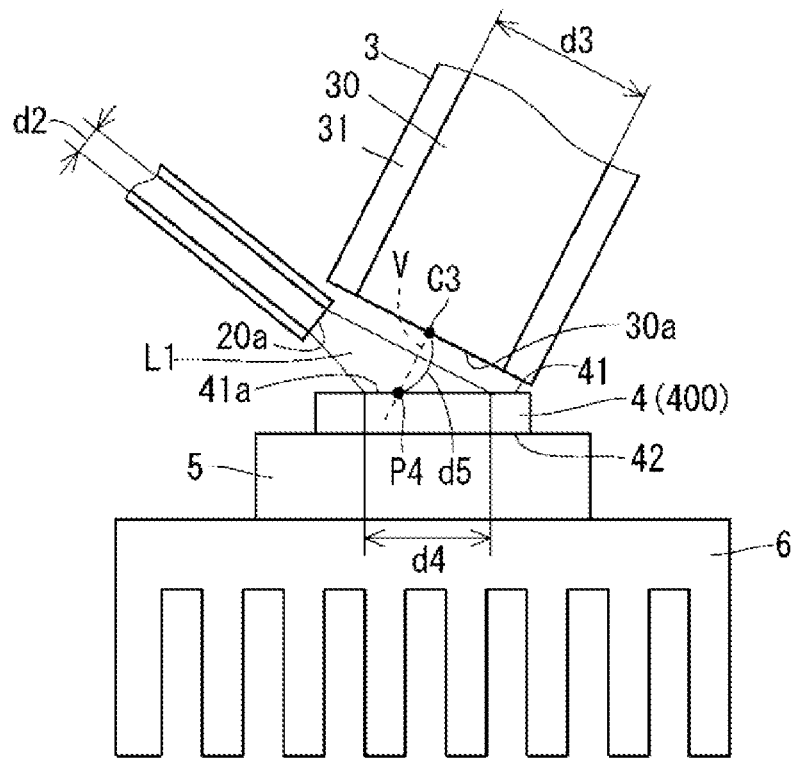
FIG. 6 is a schematic diagram of an example optical connector.

The optical fiber 3 may have a core diameter d3 greater than a core diameter d2 of the optical fiber 2, as in the example of FIG. 1 or in another example. The core diameter d3 may be smaller than the core diameter d2. The core diameter d3 may be equal to the core diameter d2. The core diameter of an optical fiber refers to the diameter of the core of the optical fiber. The core diameters d2 and d3 of the optical fibers in the example of FIG. 1 are illustrated in FIG. 5. The core diameters d2 and d3 of the optical fibers in the example of FIG. 4 are illustrated in FIG. 6. When the core diameter d3 is greater than the core diameter d2, the core diameter d3 may be, for example, 1.0 to 5.0 mm inclusive or 1.5 to 2.0 mm inclusive, and the core diameter d2 may be, for example, 0.05 to 0.8 mm inclusive or 0.1 to 0.2 mm inclusive.

As illustrated in FIGS. 1 to 6, the use of the optical fiber 3 with the core diameter d3 greater than the core diameter d2 of the optical fiber 2 increases the intensity of the conversion light L2 input into the optical fiber 3. The conversion light L2 is thus efficiently input into the optical fiber 3.

The numerical aperture of the optical fiber 3 for the conversion light L2 (also referred to as the numerical aperture of the optical fiber 3) may be greater than the numerical aperture of the optical fiber 2 for the laser light L1 (also referred to as the numerical aperture of the optical fiber 2). The numerical aperture of the optical fiber 3 may be less than the numerical aperture of the optical fiber 2. The numerical aperture of the optical fiber 3 may be equal to the numerical aperture of the optical fiber 2. When the numerical aperture of the optical fiber 3 is greater than the numerical aperture of the optical fiber 2, the numerical aperture of the optical fiber 3 may be, for example, 0.38 to 0.90 inclusive, and the numerical aperture of the optical fiber 2 may be, for example, 0.15 to 0.30 inclusive.

The use of an optical fiber 3 with a numerical aperture greater than the numerical aperture of the optical fiber 2 increases the intensity of the conversion light L2 input into the optical fiber 3. The conversion light L2 is thus efficiently input into the optical fiber 3. In other words, the use of an optical fiber 2 with a numerical aperture not greater than the numerical aperture of the optical fiber 3 reduces a spot diameter d4 of the laser light L1 in the illumination area 41a. Reducing the spot diameter d4 reduces the emission diameter of the conversion light L2 in the wavelength converter 4. The conversion light L2 is thus efficiently input into the optical fiber 3. FIGS. 5 and 6 also illustrate the spot diameter d4. The spot diameter is the diameter of the area receiving the laser light L1 or other light, which can be calculated by, for example, obtaining an image of the area receiving the light with, for example, a camera.

The spot diameter d4 of the laser light L1 in the illumination area 41a may be less than or equal to the core diameter d3 of the optical fiber 3, as in the examples of FIGS. 1 to 6. The spot diameter d4 may be greater than the core diameter d3. The spot diameter d4 may be equal to the core diameter d3. A smaller spot diameter d4 indicates the output surface 20a of the light emitter 2 being closer to the wavelength converter 4.

As in the examples of FIGS. 1 to 6, the output surface 20a of the light emitter 2 is placed close to the wavelength converter 4 to cause the spot diameter d4 to be not greater than d3. This reduces the emission diameter of the conversion light L2 in the wavelength converter 4. The conversion light L2 is thus efficiently input into the optical fiber 3. In other words, the use of the optical fiber 3 with the core diameter d3 greater than the spot diameter d4 increases the intensity of the conversion light L2 input into the optical fiber 3. The conversion light L2 is thus efficiently input into the optical fiber 3.

A distance d5 between the input surface 30a of the optical fiber 3 and the wavelength converter 4 may be less than or equal to the core diameter d3 of the optical fiber 3, as in the examples of FIGS. 1 to 6. In this case, the distance d5 may be equal to the core diameter d3, or may be less than the core diameter d3. The distance d5 may be greater than the core diameter d3. FIGS. 5 and 6 also illustrate the distance d5.

In FIGS. 5 and 6, a line V is perpendicular to the input surface 30a extending from a center C3 of the input surface 30a to the wavelength converter 4, and a point P4 is the point of intersection between the line V and the surface 40 of the wavelength converter 40. The distance d5 is the linear distance from the center C3 of the input surface 30a to the point P4.

As in the examples of FIGS. 1 to 6, the input surface 30a of the optical fiber 3 is placed close to the wavelength converter 4 to cause the distance d5 between the input surface 30a and the wavelength converter 4 to be not greater than the core diameter d3 of the optical fiber 3. This increases the intensity of the conversion light L2 input into the optical fiber 3. The conversion light L2 is thus efficiently input into the optical fiber 3. In other words, the core diameter d3 of the optical fiber 3 is set to a value greater than the distance d5 between the input surface 30a and the wavelength converter 4 to increase the intensity of the conversion light L2 input into the optical fiber 3. The conversion light L2 is thus efficiently input into the optical fiber 3.

Figure 7:
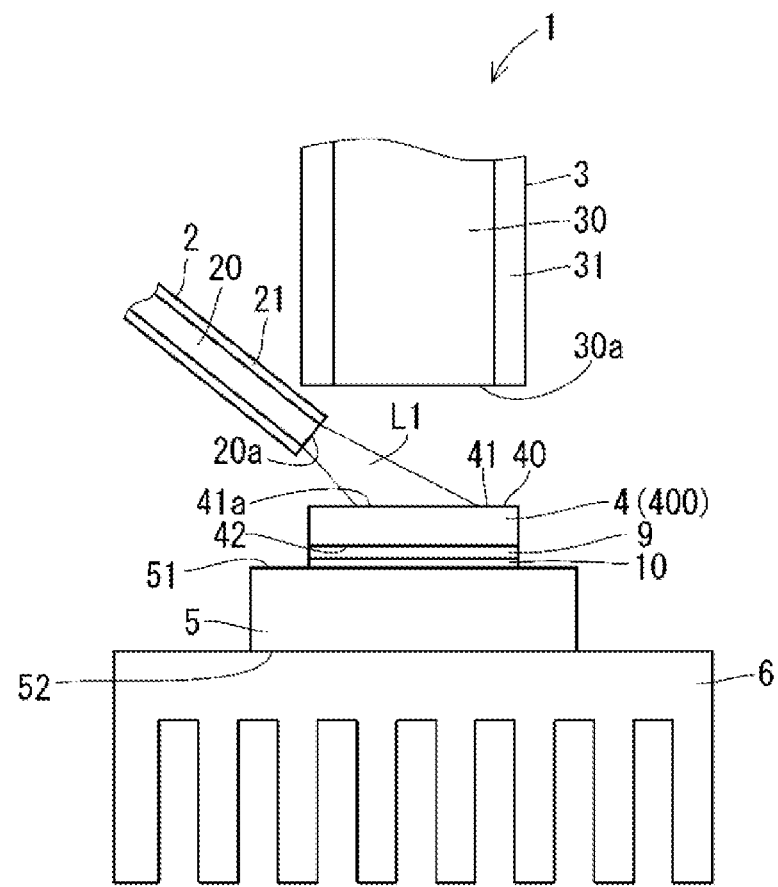
FIG. 7 is a schematic diagram of an example optical connector.

The wavelength converter 4 may be bonded to the substrate 5 with a method other than in the above examples. For example, the wavelength converter 4 may be bonded to the substrate 5 by placing a metal film 9 in the second area 42 of the wavelength converter 4 and soldering the substrate 5 to the metal film 9. FIG. 7 is a schematic diagram of an example optical connector 1 in this case.

The metal film 9 is, for example, deposited on the second area 42 of the wavelength converter 4. The metal film 9 is located on the second area 42. A solder layer 10 between the metal film 9 and the heat dissipater 6 solders the metal film 9 to the heat dissipater 6. The metal film 9 may be made of, for example, silver, aluminum, titanium, or chromium.

The metal film 9 may function as a high-reflectance member. In this case, the surface of the metal film 9 has a greater reflectance for the conversion light L2 than on the surface 40 of the wavelength converter 4. The reflectance of the surface of the metal film 9 for the conversion light L2 may be, for example, not less than 35, 40, or 50%. In another example, the reflectance of the surface of the metal film 9 for the conversion light L2 may be not less than 60, 70, or 80%.

The metal film 9 may also function as a member that reflects the laser light L1. In this case, the surface of the metal film 9 has a greater reflectance for the laser light L1 than on the surface 40 of the wavelength converter 4. The reflectance of the surface of the metal film 9 for the laser light L1 may be, for example, not less than 35, 40, or 50%. In another example, the reflectance of the surface of the metal film 9 for the laser light L1 may be not less than 60, 70, or 80%.

The reflectance of the surface of the metal film 9 for the conversion light L2 may be less than or equal to the reflectance of the surface 40 of the wavelength converter 4 for the conversion light L2. The reflectance of the surface of the metal film 9 for the laser light L1 may be less than or equal to the reflectance of the surface 40 of the wavelength converter 4 for the laser light L1.

For the surface of the metal film 9 with a greater reflectance for the conversion light L2 than on the surface 40 of the wavelength converter 4, the second component L2$b$ of the conversion light L2 has a greater intensity when being emitted from the second area 42 of the wavelength converter 4, reflected from the metal film 9, and then input into the optical fiber 3. This allows the conversion light L2 emitted from the wavelength converter 4 to be efficiently input into the light receiver 3.

For the surface of the metal film 9 with a greater reflectance for the laser light L1 than on the surface 40 of the wavelength converter 4, the transmission component of the laser light L1 has a greater intensity when being transmitted through the wavelength converter 4 and reflected from the metal film 9. Thus, the intensity of the light responsive to the transmission component emitted from the wavelength converter 4 increases. This improves the efficiency of light emission from the wavelength converter 4.

The metal film 9 may be a multilayer film. In this case, the metal film 9 may be, for example, a multilayer film including a layer of titanium, a layer of platinum, and a layer of gold stacked on one another in this order on the wavelength converter 4. In another example, the metal film 9 may be a multilayer film including a layer of chromium or silver, a layer of platinum, and a layer of gold stacked on one another in this order. In another example, the metal film 9 may be a multilayer film including a layer of chromium or silver, a layer of nickel, and a layer of gold stacked on one another in this order.

For the metal film 9 with a greater reflectance for the conversion light L2 than on the surface 40 of the wavelength converter 4, the reflectance of the substrate 5 for the conversion light L2 may be less than or equal to the reflectance of the surface 40 of the wavelength converter 4 for the conversion light L2. For the metal film 9 with a greater reflectance for the laser light L1 than on the surface 40 of the wavelength converter 4, the reflectance of the substrate 5 for the laser light L1 may be less than or equal to the reflectance of the surface 40 of the wavelength converter 4 for the laser light L1.

Figure 8:
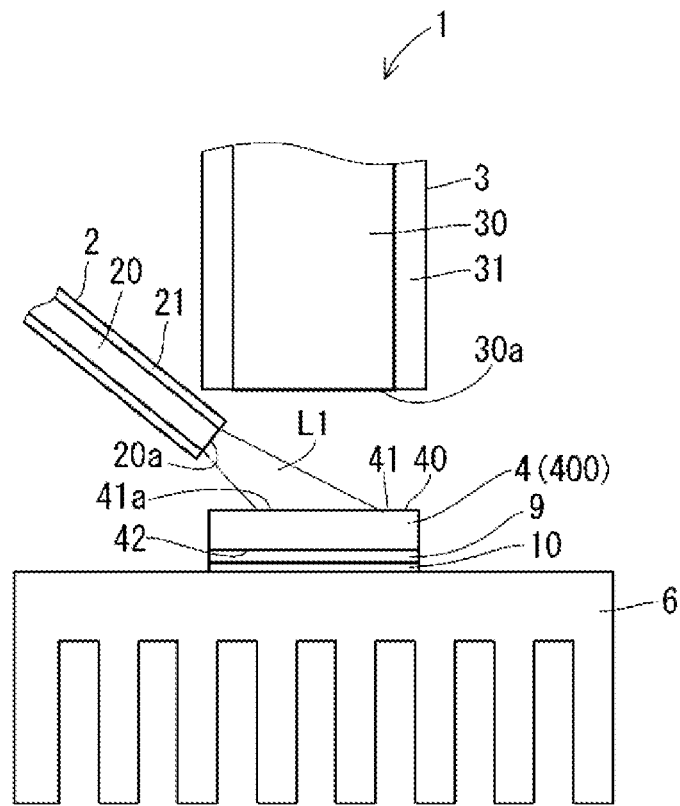
FIG. 8 is a schematic diagram of an example optical connector.

As illustrated in FIG. 8, the optical connector 1 may not include the substrate 5. In the example of FIG. 8, the metal film 9 on the second area 42 of the wavelength converter 4 is soldered to the heat dissipater 6. The solder layer 10 is located between the metal film 9 and the heat dissipater 6. In the example of FIG. 8, the surface of the metal film 9 with a greater reflectance for the conversion light L2 than on the surface 40 of the wavelength converter 4 for the conversion light L2 increases the intensity of the second component L2$b$ reflected from the metal film 9 and then input into the light receiver 3. Thus, the optical connector 1 has a less connection loss. For the surface of the metal film 9 with a greater reflectance for the laser light L1 than on the surface 40 of the wavelength converter 4, the transmission component of the laser light L1 has a greater intensity when being transmitted through the wavelength converter 4 and reflected from the metal film 9. This improves the efficiency of light emission from the wavelength converter 4.

Figure 9:
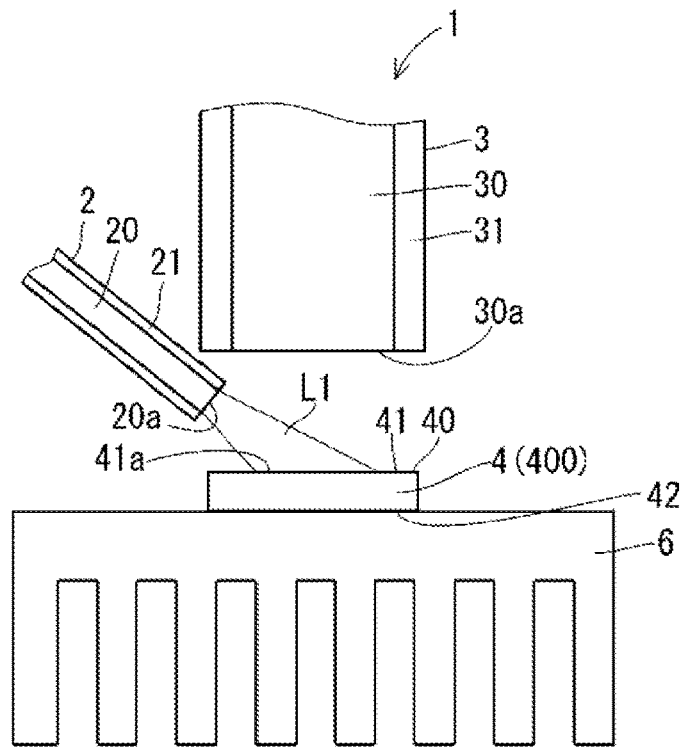
FIG. 9 is a schematic diagram of an example optical connector.

For the optical connector 1 without the substrate 5, the wavelength converter 4 may be bonded directly to the heat dissipater 6 without using a bonding material such as solder, as illustrated in FIG. 9. In the example of FIG. 9, the second area 42 of the wavelength converter 4 is bonded directly to the heat dissipater 6. The heat dissipater 6 is located on the second area 42 of the wavelength converter 4. For example, the wavelength converter 4 may be bonded directly to the heat dissipater 6 by oxygen bonding in the same or similar manner as with the bonding of the wavelength converter 4 to the substrate 5. In another example, the wavelength converter 4 may be bonded directly to the heat dissipater 6 with, for example, minute recesses and protrusions of a few micrometers on the surface of the heat dissipater 6 that anchor the wavelength converter 4.

The heat dissipater 6, when bonded directly to the wavelength converter 4, may function as a high-reflectance member. In this case, the high-reflectance member functions as a heat dissipater to dissipate heat generated by the wavelength converter 4. The surface of the heat dissipater 6 may have a greater reflectance for the conversion light L2 than on the surface 40 of the wavelength converter 4. The reflectance of the surface of the heat dissipater 6 for the conversion light L2 may be, for example, not less than 35, 40, or 50%. In another example, the reflectance of the surface of the heat dissipater 6 for the conversion light L2 may be not less than 60, 70, or 80%. For the surface of the heat dissipater 6 with a greater reflectance for the conversion light L2 than on the surface 40 of the wavelength converter 4, the second component L2$b$ has a greater intensity when being reflected from the heat dissipater 6 and then input into the light receiver 3. Thus, the optical connector 1 has a less connection loss.

The heat dissipater 6 may also function as a member that reflects the laser light L1. In this case, the surface of the heat dissipater 6 may have a greater reflectance for the laser light L1 than on the surface 40 of the wavelength converter 4. The reflectance of the surface of the heat dissipater 6 for the laser light L1 may be, for example, not less than 35, 40, or 50%. In another example, the reflectance of the surface of the heat dissipater 6 for the laser light L1 may be not less than 60, 70, or 80%. For the surface of the heat dissipater 6 with a greater reflectance for the laser light L1 than on the surface 40 of the wavelength converter 4, the transmission component of the laser light L1 has a greater intensity when being transmitted through the wavelength converter 4 and reflected from the heat dissipater 6. This improves the efficiency of light emission from the wavelength converter 4.

The wavelength converter 4 may be bonded to the heat dissipater 6 using, for example, a bonding material made of a transparent resin transmissive to the laser light L1 and the conversion light L2 instead of being bonded directly to the heat dissipater 6. In this case as well, for the surface of the heat dissipater 6 with a greater reflectance for the conversion light L2 than on the surface of the wavelength converter 4, the optical connector 1 has a less connection loss. The surface of the heat dissipater 6 with a greater reflectance for the laser light L1 than on the surface 40 of the wavelength converter 4 improves the efficiency of light emission from the wavelength converter 4.

The reflectance of the high-reflectance member for the conversion light L2 may not be greater than the reflectance of the surface 40 of the wavelength converter 4 for the conversion light L2 across the entire surface of the high-reflectance member. For example, the area of the surface of the high-reflectance member with a greater reflectance for the conversion light L2 than on the surface 40 of the wavelength converter 4 may be the area receiving the second component L2b of the conversion light L2 alone. The reflectance of the high-reflectance member for the laser light L1 may not be greater than the reflectance of the surface 40 of the wavelength converter 4 for the laser light L1 across the entire surface of the high-reflectance member. For example, the area of the surface of the high-reflectance member with a greater reflectance for the laser light L1 than on the surface 40 of the wavelength converter 4 may be the area receiving the component of the laser light L1 transmitted through the wavelength converter 4 alone. When, for example, the substrate functions as a high-reflectance member as in the examples of FIG. 1 and other figures, and is made of an aluminum alloy or aluminum, the areas of the surface 50 of the substrate 5 other than the illumination area 51a may have a black anodized finish to enhance the heat dissipation of the substrate 5. The area with a black anodized finish is colored in black and absorbs the conversion light L2 and the laser light L1. This causes the illumination area 51a alone on the surface 50 of the substrate 5 to have a greater reflectance for the conversion light L2 than on the surface 40 of the wavelength converter 4. This also causes the illumination area 51a alone on the surface 50 of the substrate 5 to have a greater reflectance for the laser light L1 than on the surface 40 of the wavelength converter 4. The same or similar finish may be applied to the metal film 9 that functions as a high-reflectance member. The same or similar finish may be applied to the heat dissipater 6 that functions as a high-reflectance member.

Although the optical connector 1 includes the heat dissipater 6 in each of the above examples, the optical connector 1 may not include the heat dissipater 6.

Figure 10:
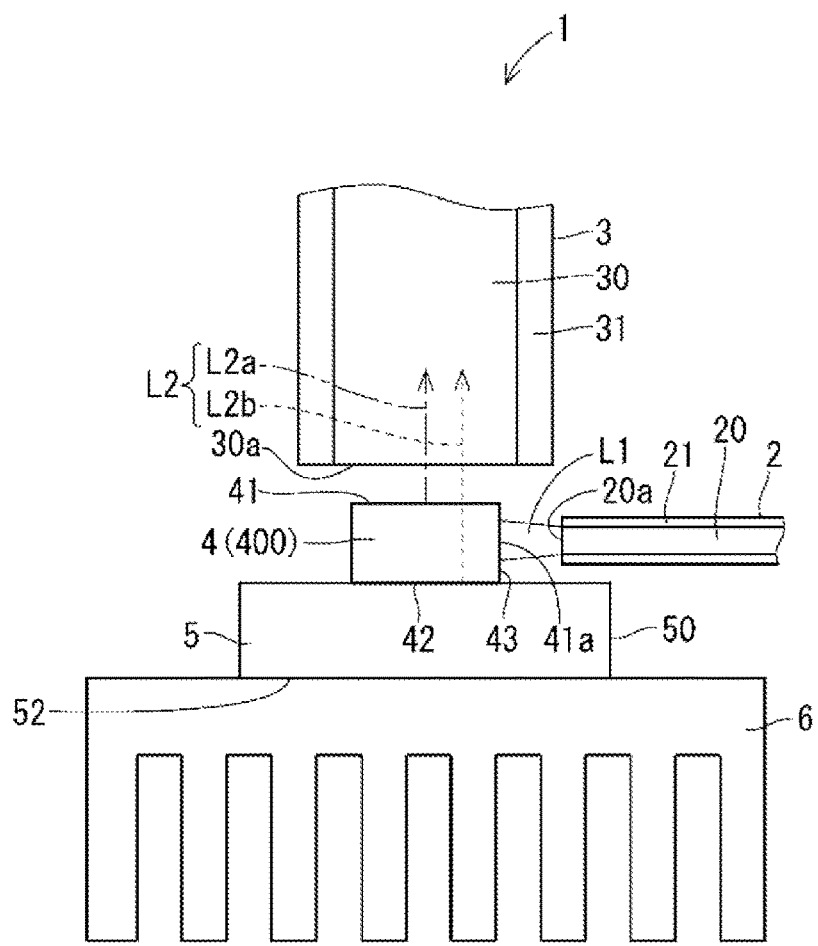
FIG. 10 is a schematic diagram of an example optical connector.

Although the laser light L1 is applied to the first main surface 41 of the surface 40 of the wavelength converter 4 in each of the above examples, the laser light L1 may be applied to an area other than the first main surface 41. FIG. 10 illustrates an example of the laser light L1 being applied to a peripheral side surface 43 connecting the first main surface 41 and the second main surface 42 included in the surface 40 of the wavelength converter 4. In the example of FIG. 10, the illumination area 41a is included in the peripheral side surface 43. In the example of FIG. 10, the conversion light L2 includes, for example, the first component L2a emitted directly from the wavelength converter 4 and input directly into the optical fiber 3 from the first main surface 41 of the wavelength converter 4. In the example of FIG. 10 as well, the conversion light L2 emitted from the wavelength converter 4 directly travels to the light receiver 3, eliminating the optical system for input described above. This simplifies the assembly process of the optical connector 1. This further simplifies the structure of the optical connector 1.

Figure 11:
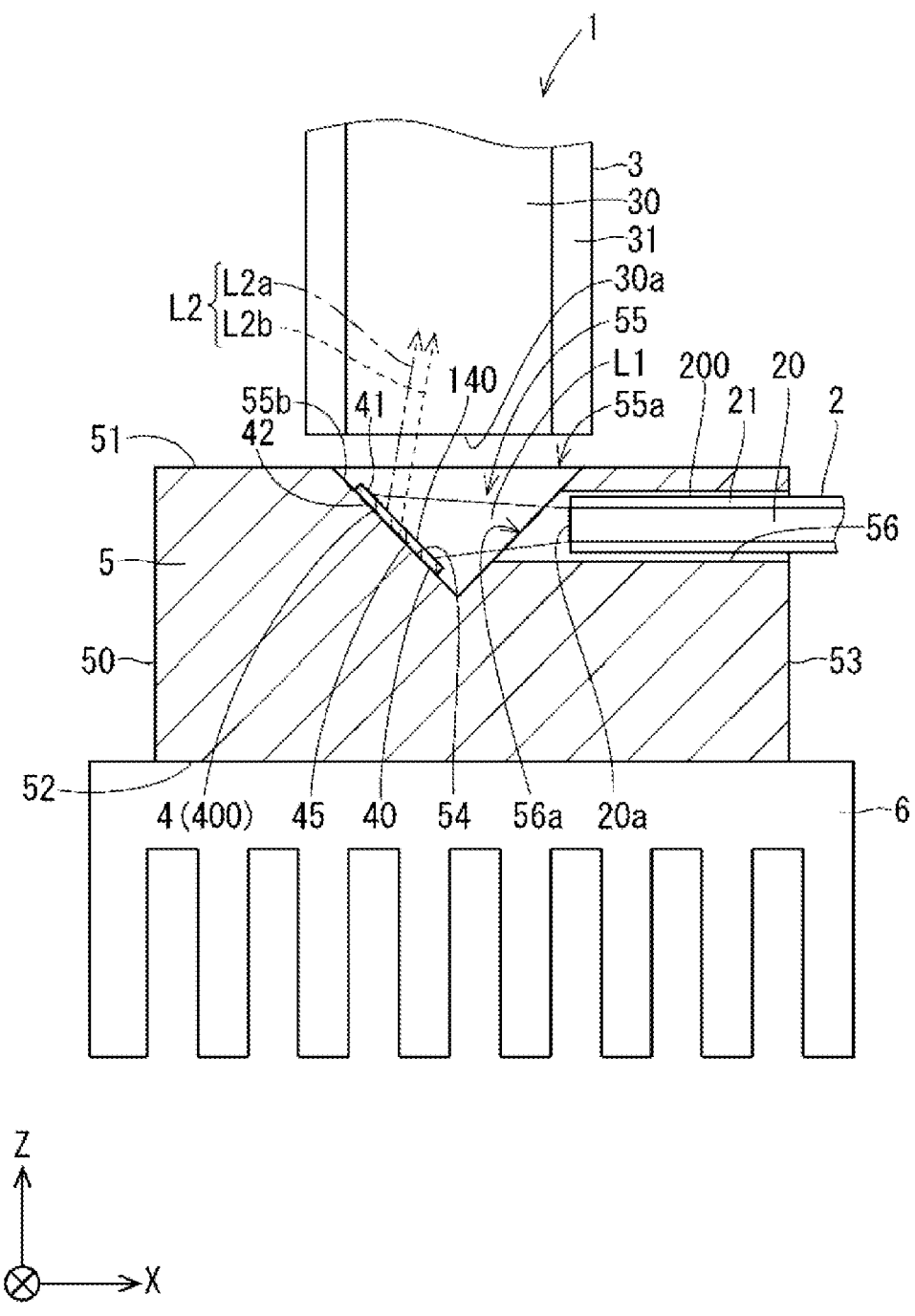
FIG. 11 is a schematic diagram of an example optical connector.
Figure 12:
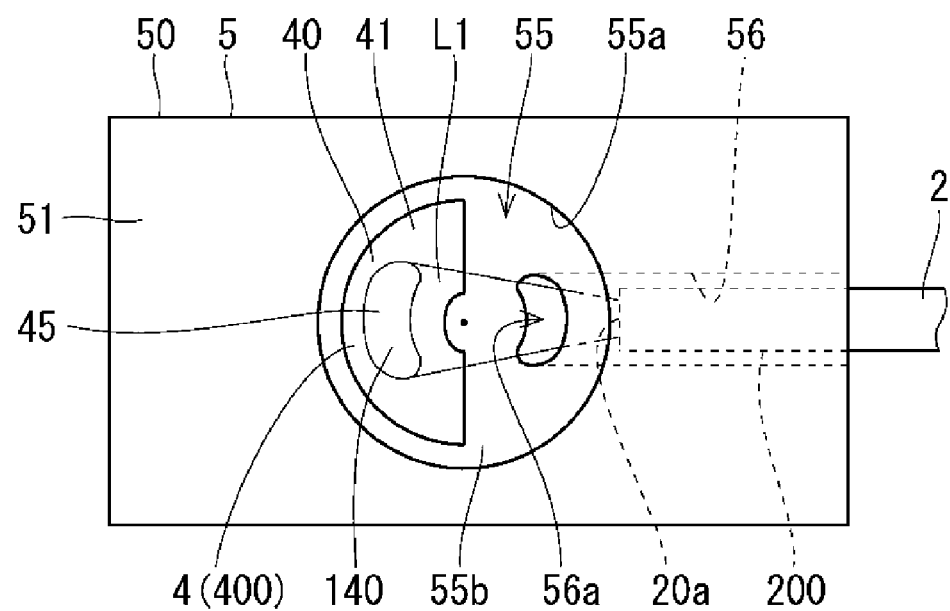
FIG. 12 is a schematic diagram of an example optical connector.

FIG. 11 is a schematic diagram of another example optical connector 1. FIG. 12 is a schematic diagram of examples of the wavelength converter 4, the substrate 5, and the light emitter 2 included in the optical connector 1. The optical connector 1 will now be described with reference to the XYZ orthogonal coordinate system illustrated in FIGS. 11 and 12. The negative Z-direction herein is downward. The positive Z-direction is upward. The light emitter 2 is, for example, an optical fiber. The optical fiber 2 is, for example, located in the positive X-direction from the wavelength converter 4. In the example of FIGS. 11 and 12, the optical fiber 2 extends in, for example, X-direction. Although an example of the light emitter 2 that is an optical fiber 2 will now be described, the structure is not limited to this example. The light emitter 2 may be a laser element alone or a laser element mounted in a can package.

The optical fiber 2 includes an output end 200 including an output surface 20a through which the laser light L1 is output. The core 20, for example, includes the output surface 20a. The output surface 20a is, for example, a circular flat surface and may also be referred to as an output end face. The output surface 20a is located near the wavelength converter 4. The output surface faces toward the wavelength converter 4. At least a portion of the laser light L1 output through the output surface 20a travels directly to the wavelength converter 4 without being reflected from, for example, another member. The laser light L1 is output through the output surface 20a, for example, in the negative X-direction.

The surface 40 of the wavelength converter 4 includes an illumination area 140 that receives the laser light L1. In the example of FIG. 11, the illumination area 140 is included in the first surface 41 of the wavelength converter 4. The laser light L1 travels directly to the first surface 41. The illumination area 140 can be identified by, for example, obtaining images with a measurement device based on light emission and reception.

The surface 40 of the wavelength converter 4 includes the first area on which a member that reflects the light L2 is located. In other words, the first area included in the surface 40 is located on a member that reflects the light L2. In this example, the first area is, for example, the second surface 42. The member that reflects the light L2 is located on the second surface 42. The member located on the surface 40 of the wavelength converter 4 to reflect the light L2 may be hereafter referred to as a high-reflectance member. The light L2 may be referred to as conversion light L2. In this example, the substrate 5 is a high-reflectance member. The substrate 5 is located on the second surface 42 of the wavelength converter 4. The high-reflectance member may reflect the laser light L1, in addition to the conversion light L2.

In the present embodiment, the substrate 5 is, for example, a substantially rectangular prism. The surface 50 of the substrate 5 includes an upper surface 51 and a lower surface 52 that are flat and face each other, and a peripheral side surface 53 connecting the upper surface 51 and the lower surface 52. The upper surface 51 and the lower surface 52 are, for example, parallel to the XY plane.

In the present embodiment, the substrate 5 includes a recess 55. The recess 55 includes an opening 55a (also referred to as a second opening) that is open on the surface 50 of the substrate 5. The opening 55a is open, for example, in the upper surface 51 of the substrate 5.

The wavelength converter 4 is located in the recess 55. The second surface 42 of the wavelength converter 4 is bonded to, for example, an inner surface 55b (or the inner wall) of the recess 55. The wavelength converter 4 is shaped in conformance with the inner surface 55b of the recess 55. The inner surface 55b of the recess 55 is, for example, conical. An opening 56a of the recess 55 is, for example, circular. The wavelength converter 4 is curved in conformance with the conical shape of the inner surface 55b of the recess 55.

In the optical fiber 2, at least the output end 200 overlaps the substrate 5 in a transparent plan view. In the optical fiber 2, at least the output end 200 may be embedded in the substrate 5. In other words, at least the output end 200 of the optical fiber 2 may be located in a hole 56 in the substrate 5, or in a groove 57 described below. At least the output end 200 of the optical fiber 2 may be located on the upper surface of the substrate 5, with the output end 200 covered with, for example, a metal plate of the same material as the substrate 5, a metal plate of a different material from the substrate 5, or a resin adhesive. The substrate 5 includes the hole 56 in which at least the output end 200 of the optical fiber 2 is embedded. The hole 56 extends, for example, in X-direction, from the peripheral side surface 53 of the substrate 5 to the recess 55. The hole 56 is open on the peripheral side surface 53 of the substrate 5. The hole 56 connects with a space in the recess 55 on the substrate 5. The hole 56 includes the opening 56a (also referred to as a first opening) connecting with the space in the recess 55 on the substrate 5. The output surface 20a of the output end 200 faces toward the opening 56a. The optical fiber 2 is placed into the hole 56 through the opening of the hole 56 on the peripheral side surface 53.

The wavelength converter 4 is located on the inner surface 55b of the recess 55 to cover, for example, most of the half (in the negative X-direction) opposite to the half (in the positive X-direction) with the opening 56a of the hole 56. The laser light L1 output through the output surface 20a travels through the opening 56a of the hole 56 directly to the upper surface 51 of the wavelength converter 4 in the recess 55. The wavelength converter 4 includes an illuminating portion 45 that directly receives the laser light L1.

The light receiver 3 transmits the input conversion light L2. The light receiver 3 is, for example, an optical fiber, and the cross section of the optical fiber 3 taken perpendicularly to its axial direction is, for example, circular. Although the light receiver 3 is the optical fiber 3 in the example described below, the light receiver 3 may not be an optical fiber. The light receiver 3 may also be, for example, a rod lens, an integrator lens, a hollow mirror, or a light guide. The optical fiber 3 is, for example, located in the positive Z-direction from the wavelength converter 4 and the optical fiber 2. The optical fiber 3 extends in, for example, Z-direction. The optical fiber 2 and the optical fiber 3 are located not to cross each other.

The input surface 30a faces, for example, the opening 55a of the recess 55 on the substrate 5. The input surface 30a faces, for example, an open face of the opening 55a. The input surface 30a is, for example, parallel to the open face of the recess 55 (specifically, the face outlined by the opening 55a). When, for example, the recess 55 is viewed from the opening 55a in Z-direction (or the direction of thickness of the substrate 5), the wavelength converter 4 (specifically the first surface 41 of the wavelength converter 4) is visible (refer to FIG. 12). The area of the input surface 30a may be larger than, smaller than, or equal to the opening area of the recess 55 (specifically, the area of the face outlined by the opening 55a).

The conversion light L2 emitted from the wavelength converter 4 includes, for example, the first component L2a emitted directly from the wavelength converter 4 and input directly into the optical fiber 3 through the opening 55a of the recess 55. In the examples of FIGS. 11 and 12, the conversion light L2 includes, for example, the first component L2a emitted directly from the illumination area 140 of the wavelength converter 4 and input directly into the optical fiber 3 through the opening 55a. The first component L2a is a component of the conversion light L2 input into the optical fiber 3 without being reflected from a member other than the wavelength converter 4.

The conversion light L2 further includes the second component L2b emitted from the first area located on the substrate 5 and included in the surface 40 of the wavelength converter 4, reflected from the substrate 5, and then input into the optical fiber 3. In this example, the second component L2b is a component of the conversion light L2 emitted from the second area 42 of the wavelength converter 4, reflected from the substrate 5, and then input into the optical fiber 3. The second component L2b is reflected from the inner surface 55b of the recess 55 on the substrate 5, transmitted through the wavelength converter 4, and is then input into the optical fiber 3. The second component L2b includes a component transmitted through the wavelength converter 4, emitted from the illumination area 140, and input directly into the optical fiber 3. The surface 50 of the substrate 5 includes an illumination area 54 that receives the second component L2b. In the example of FIGS. 11 and 12, the illumination area 54 is included in the inner surface 55b of the recess 55.

The conversion light L2 also includes a component not input into the optical fiber 3, in addition to the first component L2a and the second component L2b. The conversion light L2 may include a component input into the optical fiber 3, other than the first component L2a or the second component L2b. For example, the conversion light L2 may include a component reflected from an area of the inner surface 55b of the recess 55 without including the wavelength converter 4 (for example, the half in the positive X-direction with the opening 56a of the hole 56) and then input into the optical fiber 3.

The laser light L1 output from the optical fiber 2 includes a transmission component that is transmitted through the wavelength converter 4 and reaches the illumination area 54 of the substrate 5. The transmission component is reflected from the illumination area 54 of the substrate 5 back to the wavelength converter 4. The wavelength converter 4 then emits light in response to the transmission component. This light may be referred to as light responsive to the transmission component. A portion of the light responsive to the transmission component is emitted from the illumination area 140 as part of the first component L2a and is input directly into the optical fiber 3. A portion of the light responsive to the transmission component is output from the second area 42 as part of the second component L2b and is input into the optical fiber 3 after being reflected from the substrate 5.

As described above, in the optical connector 1 in this example, at least the output end 200 of the optical fiber 2 is embedded in the substrate 5. This allows the optical connector 1 to occupy a smaller space than in a structure with the entire optical fiber 2 located outside the substrate 5.

With at least the output end 200 of the optical fiber 2 embedded in the substrate 5, the input surface 30a of the optical fiber 3 is less likely to interfere with the output end 200 of the optical fiber 2 when placed closer to the wavelength converter 4 from outside the substrate 5. This facilitates placing the input surface 30a of the optical fiber 3 closer to the wavelength converter 4. This allows the conversion light L2 emitted from the wavelength converter 4 to reach the optical fiber 3 easily and thus to be efficiently input into the optical fiber 3.

In this example, embedding at least the output end 200 of the optical fiber 2 in the hole 56 in the substrate 5 further allows the output end 200 to be positioned by placing the output end 200 in the hole 56. This facilitates positioning of the output end 200.

In this example, the wavelength converter 4 located in the recess 55 on the substrate 5 further reduces the space for accommodating the optical connector 1.

In this example, the laser light L1 travels directly from the optical fiber 2 to the wavelength converter 4. This eliminates, for example, an optical system including, for example, an optical mirror (also referred to as an optical system for laser application) to direct the laser light L1 to the wavelength converter 4. Unlike in this example, an optical connector 1 including an optical system for laser application involves adjusting the positions of each component of the optical system for laser application in assembling the optical connector 1. This may complicate the assembly process of the optical connector 1. The optical connector 1 in this example eliminates an optical system for laser application and thus simplifies the assembly process of the optical connector 1. This further simplifies the structure of the optical connector 1.

In this example, the conversion light L2 emitted from the wavelength converter 4 directly travels to the optical fiber 3. This eliminates, for example, an optical system including, for example, an optical mirror (also referred to as an optical system for fiber input) to direct the conversion light L2 to the optical fiber 3. Unlike in this example, an optical connector 1 including an optical system for fiber input involves adjusting the positions of each component of the optical system for fiber input in assembling the optical connector 1. This may complicate the assembly process of the optical connector 1. The optical connector 1 in this example eliminates an optical system for fiber input and thus simplifies the assembly process of the optical connector 1. This further simplifies the structure of the optical connector 1.

In this example, the input surface 30a of the optical fiber 3 facing the opening 55a of the recess 55 in which the wavelength converter 4 is located also increases the intensity of the component of conversion light L2 emitted from the wavelength converter 4 and directly input into the optical fiber 3 after passing through the opening 55a of the recess 55. The conversion light L2 is thus efficiently input into the optical fiber 3. Thus, the optical connector 1 has a less connection loss.

The structure and the configuration of the optical connector 1 are not limited to the above examples. The inner surface 55b of the recess 55 on the substrate 5 may be, for example, in any shape other than being conical. The inner surface 55b may be, for example, pyramidal or partially spherical (e.g., hemispherical). The inner surface 55b may be truncated conical with the side surface and the upper surface (also referred to as the top), or be truncated conical with the side surface and the bottom surface. The inner surface 55b may be truncated pyramidal with the side surfaces and the upper surface, or be truncated pyramidal with the side surfaces and the bottom surface.

In the substrate 5, a half or more of the optical fiber 2 may be embedded, most of the optical fiber 2 may be embedded, or the optical fiber 2 may be embedded entirely.

Figure 13:
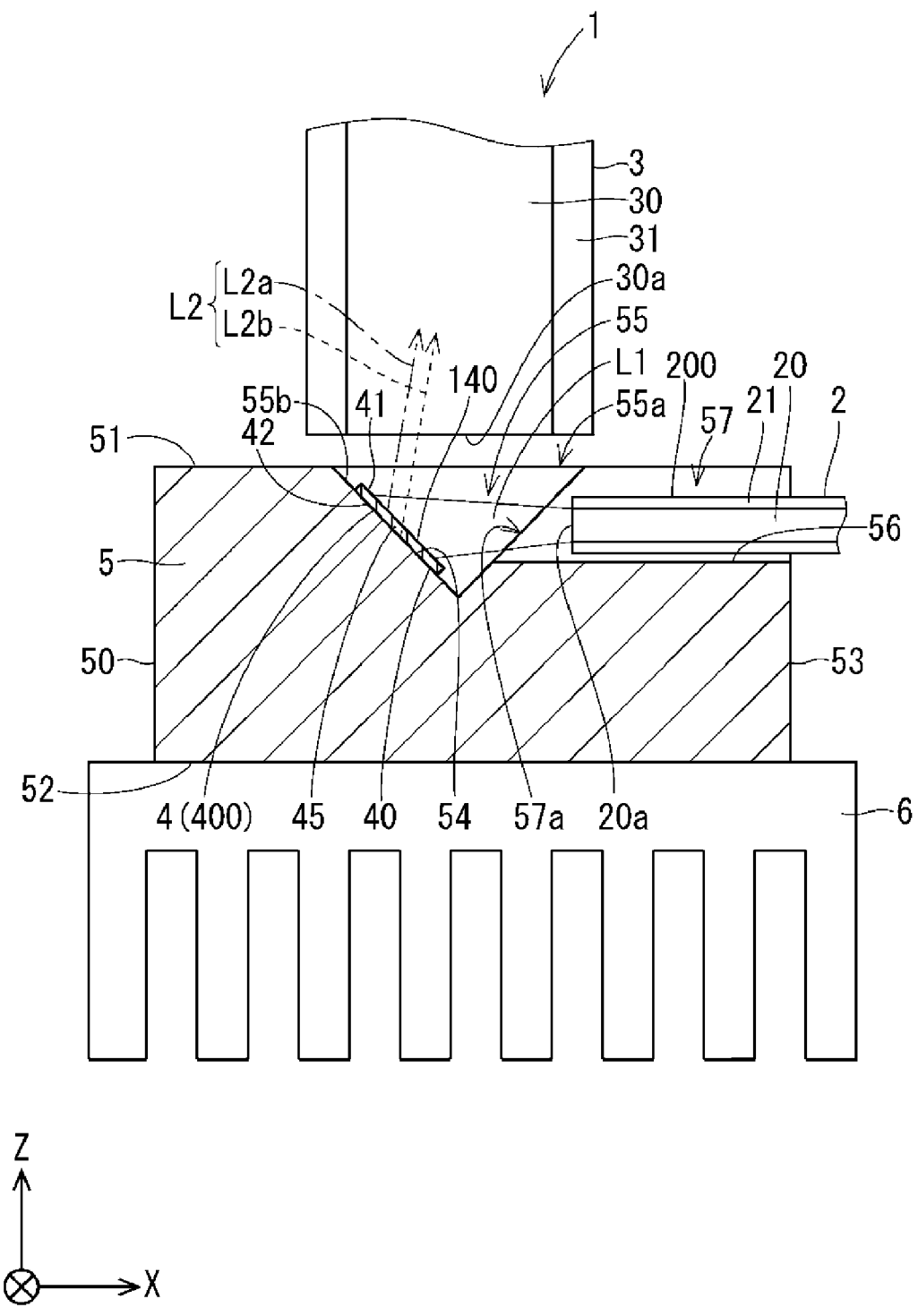
FIG. 13 is a schematic diagram of an example optical connector.
Figure 14:
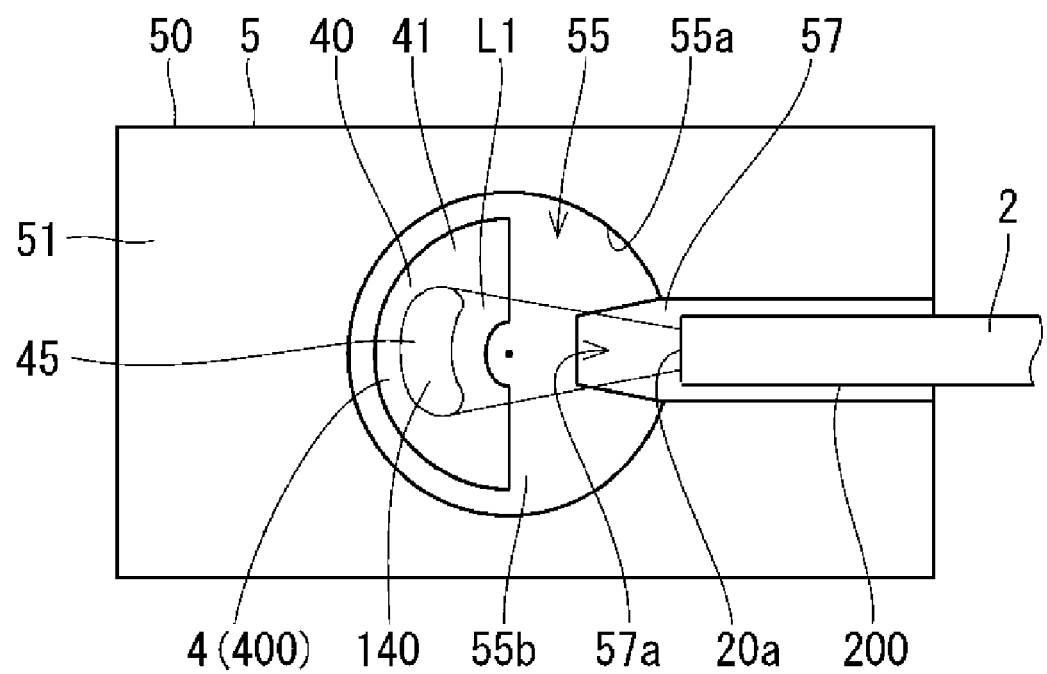
FIG. 14 is a schematic diagram of an example optical connector.

The optical fiber 2 may be embedded in the substrate 5 with a method other than the above. For example, at least the output end 200 of the optical fiber 2 may be embedded in the groove 57 on the substrate 5. FIG. 13 is a schematic diagram of an example optical connector 1 in this case. FIG. 14 is a schematic diagram of examples of the wavelength converter 4, the substrate 5, and the optical fiber 2 illustrated in FIG. 13 as viewed in the positive Z-direction.

As illustrated in FIGS. 13 and 14, the substrate 5 includes the groove 57 in which at least the output end 200 of the optical fiber 2 is embedded. The groove 57 extends, for example, in X-direction from the peripheral side surface 53 of the substrate 5 to the recess 55 on the substrate 5. The groove 57 connects with a space in the recess 55. The groove 57 is open both on the upper surface 51 and on the peripheral side surface 53. The groove 57 includes an opening 57a (also referred to as a first opening) connects with the space in the recess 55 on the substrate 5. The laser light L1 output through the output surface 20a of the optical fiber 2 travels through the opening 57a directly to the upper surface 51 of the wavelength converter 4 in the recess 55.

As illustrated in FIGS. 13 and 14, embedding at least the output end 200 of the optical fiber 2 in the groove 57 allows the output end 200 to be positioned by placing the output end 200 in the groove 57. This facilitates positioning of the output end 200.

Figure 15:
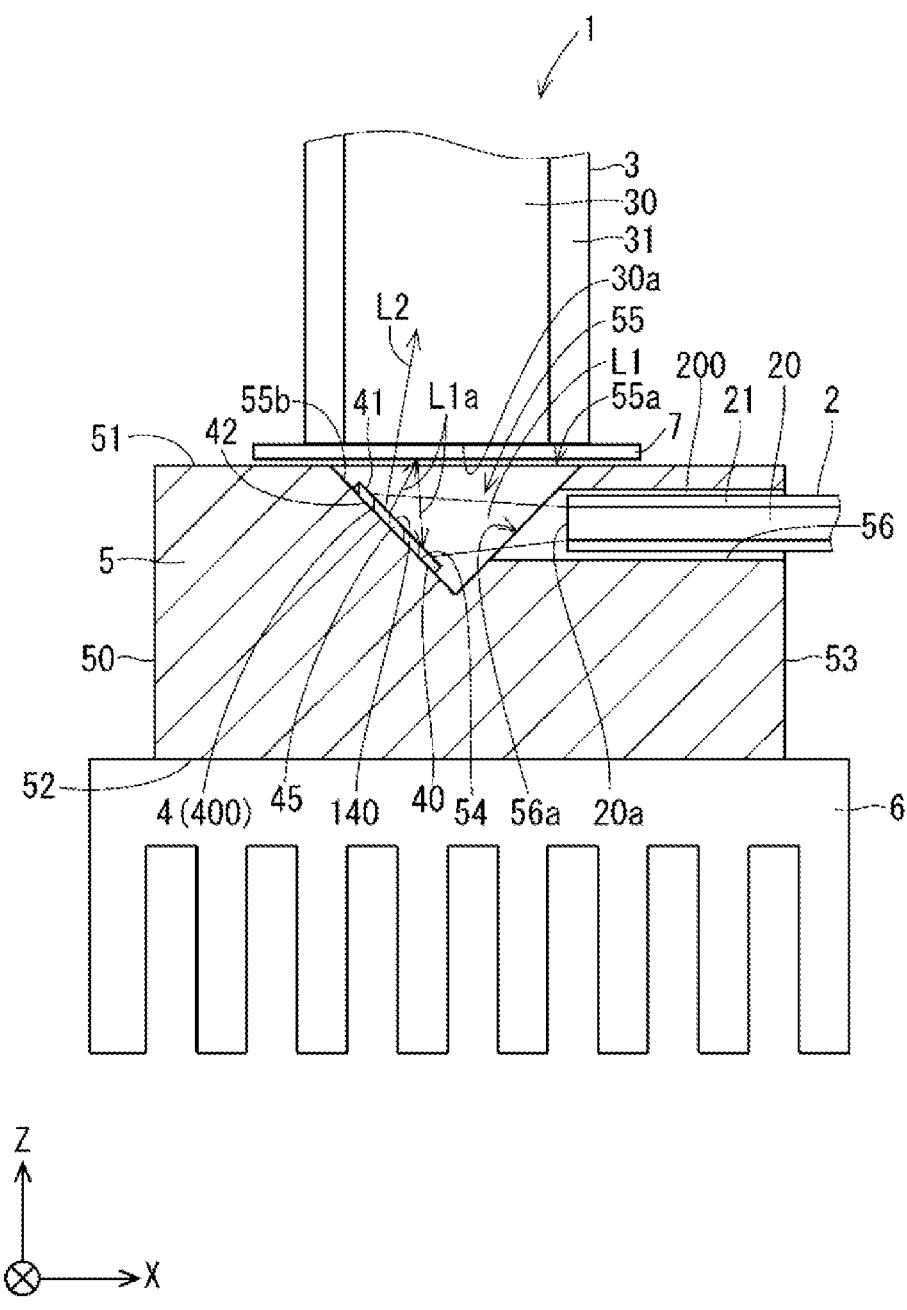
FIG. 15 is a schematic diagram of an example optical connector.
Figure 16:
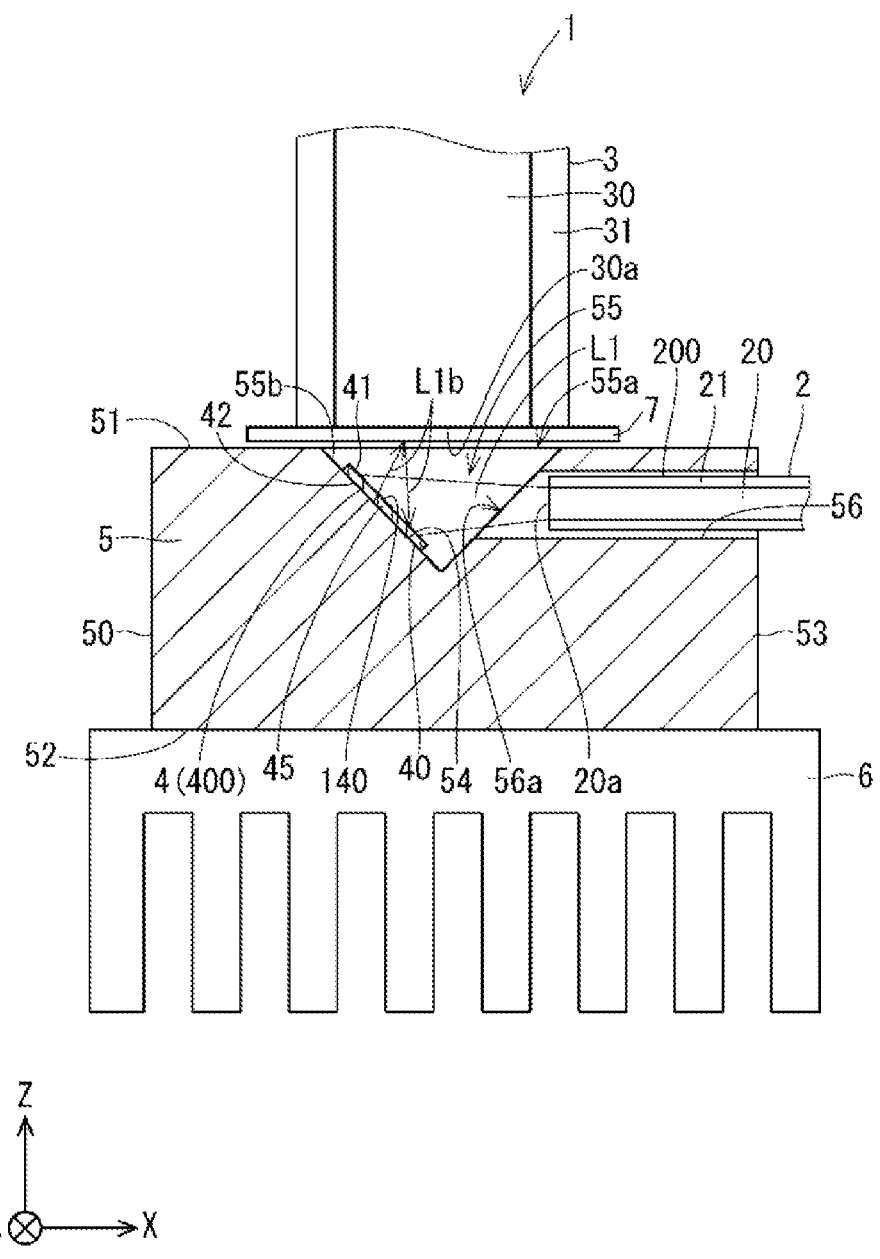
FIG. 16 is a schematic diagram of an example optical connector.

The optical connector 1 may include an optical filter 7 (also referred to as a first optical filter) that covers at least a portion of the opening 55a of the recess 55. The optical filter 7 reflects the laser light L1 and transmits the conversion light L2. FIGS. 15 and 16 are schematic diagrams of an example optical connector 1 including the optical filter 7. The optical connectors 1 illustrated in FIGS. 15 and 16 are identical to each other.

In the example of FIGS. 15 and 16, the optical filter 7 covers, for example, the entire area of the opening 55a of the recess 55. The optical filter 7 is, for example, a plate, a sheet, or a film. The optical filter 7 is, for example, planar along the XY plane. The optical filter 7 may have a thickness of, for example, 0.05 to 0.5 mm inclusive. The optical filter 7 is located between, for example, the input surface 30a of the optical fiber 3 and the opening 55a of the recess 55. The optical filter 7 is, for example, in contact with the entire area of the input end face of the optical fiber 3. The optical filter 7 is, for example, in contact with the input surface 30a of the core 30 and the input end face of the cladding 31.

The optical filter 7 that transmits the conversion light L2 causes the conversion light L2 emitted from the wavelength converter 4 to transmit through the optical filter 7 and reach the input surface 30a of the optical fiber 3. The optical filter 7 also reflects the laser light L1. The optical filter 7 thus reflects, for example, a first reflected component L1a of the laser light L1 reflected from the surface 40 of the wavelength converter 4 back to the wavelength converter 4, as illustrated in FIG. 15. In the example of FIG. 15, the optical filter 7 reflects, for example, the first reflected component L1a of the laser light L1 that is reflected from the first surface 41 of the wavelength converter 4 back to the first surface 41 of the wavelength converter 4.

As illustrated in FIG. 16, the optical filter 7 reflects, for example, a second reflected component L1b of the laser light L1 transmitted through the wavelength converter 4 and reflected from the substrate 5 back to the wavelength converter 4. In the example of FIG. 16, the optical filter 7 reflects, for example, the second reflected component L1b of the laser light L1 output through the second surface 42 of the wavelength converter 4 and reflected from the illumination area 54 of the substrate 5 back to the first surface 41 of the wavelength converter 4.

The optical filter 7 may have a reflectance for the laser light L1 of, for example, not less than 80, 90, or 95%. The optical filter 7 may have a transmittance for the conversion light L2 of, for example, not less than 80, 90, or 95%. The optical filter 7 may be made of, for example, glass or a material other than glass.

The optical connector 1 including the optical filter 7 as described above allows the first reflected component L1*a* and the second reflected component L1*b* included in the laser light L1 to reach the wavelength converter 4. This improves the efficiency of light emission from the wavelength converter 4.

The optical filter 7 covering the entire area of the opening 55*a* of the recess 55, as in the example of FIGS. 15 and 16, increases the intensity of the first and second reflected components L1*a* and L1*b* reflected from the optical filter 7 back to the wavelength converter 4. This further improves the efficiency of light emission from the wavelength converter 4.

The optical filter 7, which reflects the laser light L1, covers at least a portion of the opening 55*a* of the recess 55. This further reduces the likelihood of the laser light L1 reaching the input surface 30*a* of the optical fiber 3 that is to transmit the conversion light L2.

Figure 17:
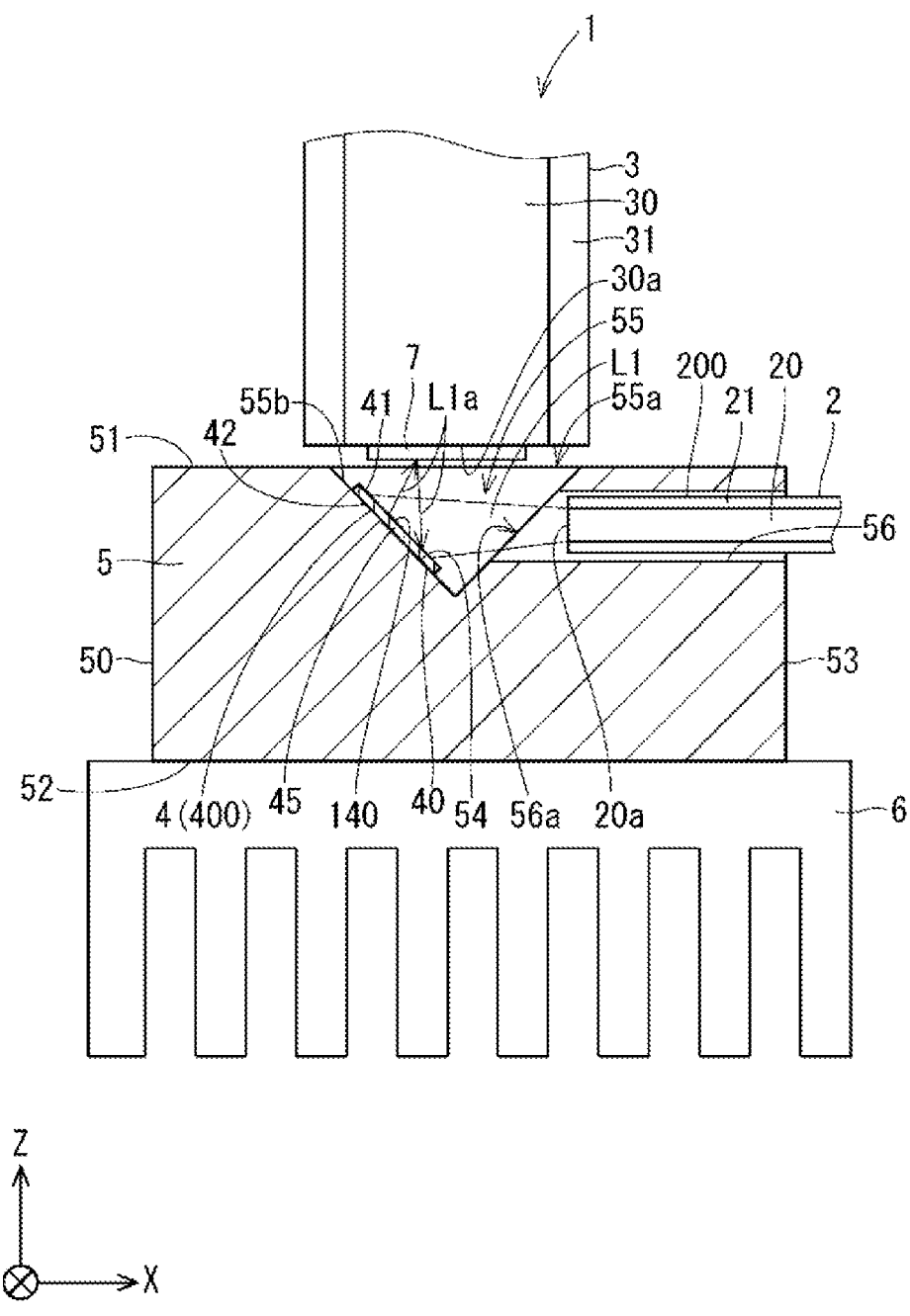
FIG. 17 is a schematic diagram of an example optical connector.

As in the example of FIG. 17, the optical filter 7 may partially cover the opening 55*a* of the recess 55. As in the example of FIG. 17, the optical filter 7 may not be in contact with the input end face of the cladding 31 of the optical fiber 3. As in the example of FIG. 17, the optical filter 7 may be partially in contact with the input surface 30*a* of the optical fiber 3. The optical filter 7 may not be in contact with the input surface 30*a* of the optical fiber 3. With the optical filter 7 in contact with the input surface 30*a*, the laser light L1 is less likely to be incident on the input surface 30*a*. Although a small clearance is left between the optical filter 7 and the upper surface 51 of the substrate 5 in the example of FIGS. 15 and 16, the optical filter 7 may be in contact with the upper surface 51. In this case, the laser light L1 is less likely to leak outside the substrate 5.

Figure 18:
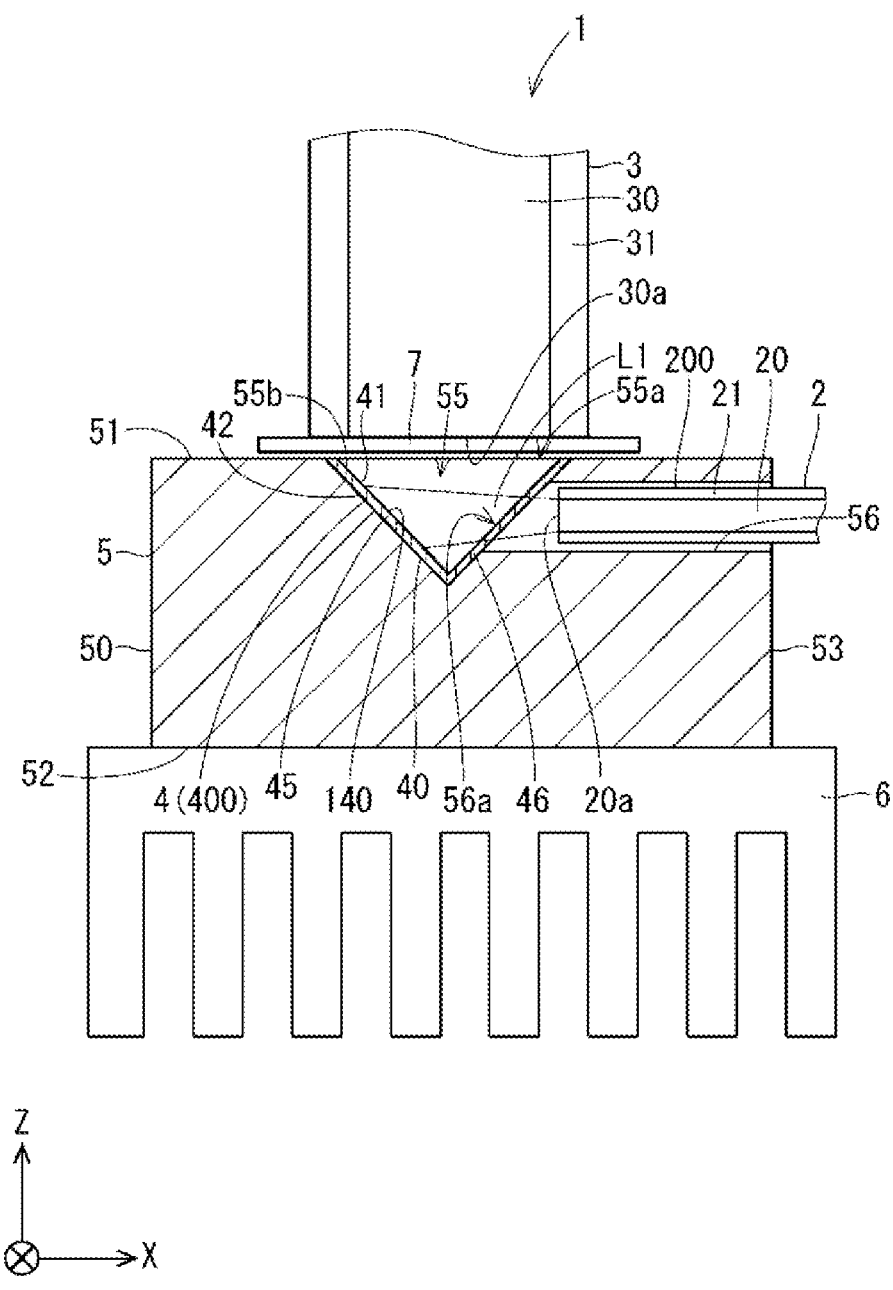
FIG. 18 is a schematic diagram of an example optical connector.
Figure 19:
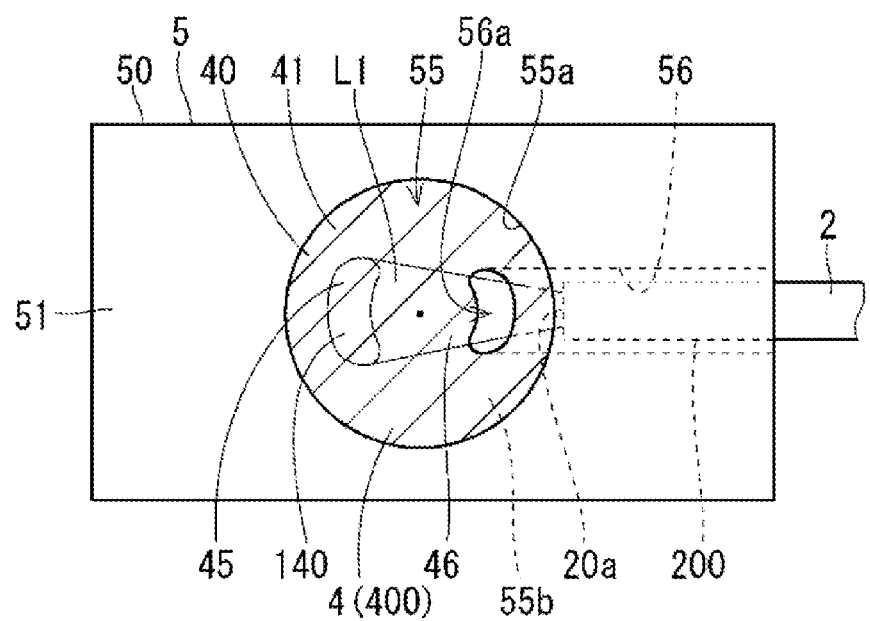
FIG. 19 is a schematic diagram of an example optical connector.

The wavelength converter 4 may be located, on the inner surface 55*b* of the recess 55 on the substrate 5, in an area other than in the above example. FIG. 18 is a schematic diagram of a wavelength converter 4 located across the entire area of the inner surface 55*b* of the recess 55. FIG. 19 is a schematic diagram of examples of the wavelength converter 4, the substrate 5, and the optical fiber 2 illustrated in FIG. 18 as viewed in the positive Z-direction. In FIG. 19, the wavelength converter 4 is hatched with diagonal lines.

In the example of FIGS. 18 and 19, the wavelength converter 4 is located across the entire area of the inner surface 55*b* of the recess 55. The wavelength converter 4 is, for example, a hollow cone with the bottom surface being open. In other words, the first surface 41 of the wavelength converter 4 is the inner surface, and the second surface 42 of the wavelength converter 4 is the outer surface. The wavelength converter 4 includes a peripheral portion 46 located on the periphery of the opening 56*a* of the hole 56, in addition to the illuminating portion 45 that directly receives the laser light L1. The periphery of the opening 56*a* herein refers to the area surrounding the opening 56*a*.

With the wavelength converter 4 including the peripheral portion 46 in addition to the illuminating portion 45 as in this example, the component of the laser light L1 reflected from the optical filter 7 is more likely to reach the wavelength converter 4. This further improves the efficiency of light emission from the wavelength converter 4.

With the wavelength converter 4 located across the entire area of the inner surface 55*b* of the recess 55 as in this example, the component of the laser light L1 reflected from the optical filter 7 is more likely to reach the wavelength converter 4. This further improves the efficiency of light emission from the wavelength converter 4.

The wavelength converter 4 may simply include the illuminating portion 45. The wavelength converter 4 may simply include the illuminating portion 45 and the peripheral portion 46. The wavelength converter 4 may be located to cover a half or more of the inner surface 55*b* of the recess 55 or may be located to cover more than two-thirds of the inner surface 55*b*.

Figure 20:
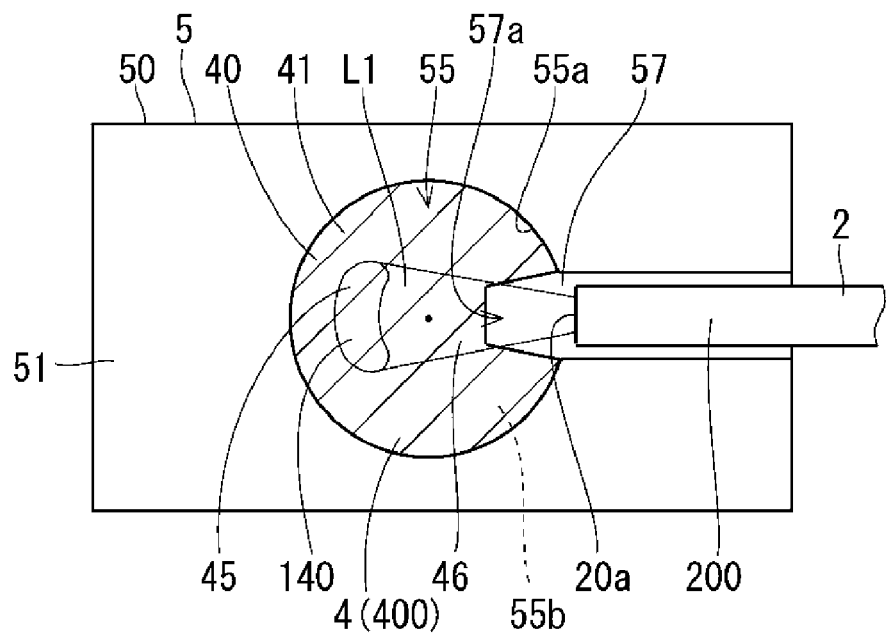
FIG. 20 is a schematic diagram of an example optical connector.
Figure 20:
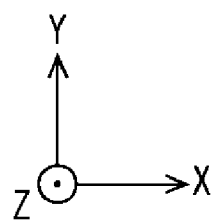

For the optical fiber 2 embedded in the groove 57 on the substrate 5, as in the example of FIGS. 13 and 14, the wavelength converter 4 may include the peripheral portion 46 around the opening 57*a* of the groove 57, in addition to the illuminating portion 45. In this structure, the wavelength converter 4 may be located across the entire area of the inner surface 55*b* of the recess as illustrated in FIG. 20.

Figure 21:
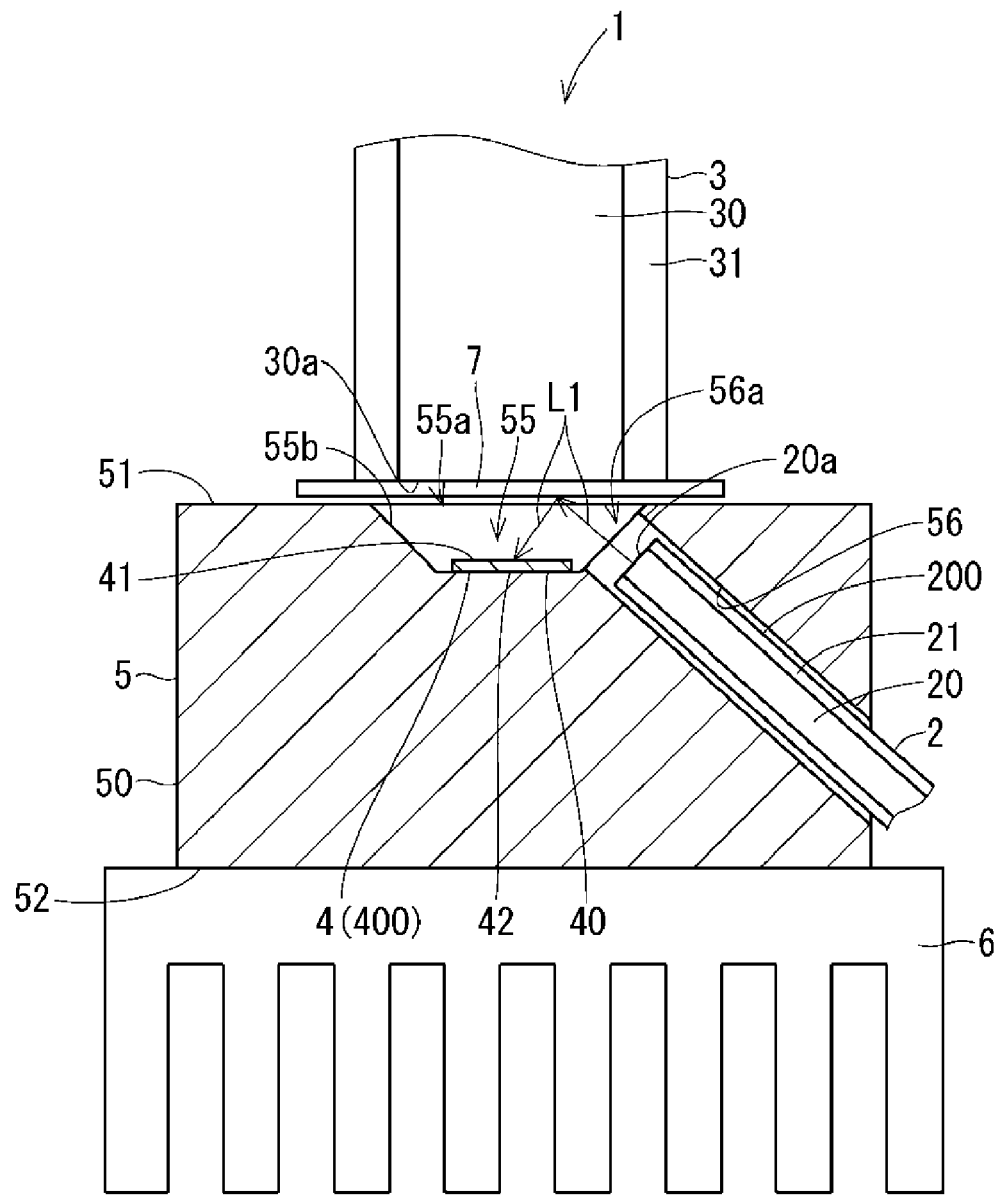
FIG. 21 is a schematic diagram of an example optical connector.

Although the laser light L1 is applied directly to the wavelength converter 4 in each of the above examples, the laser light L1 may be applied with reflection from another member. FIG. 21 is a schematic diagram of an example optical connector 1 in this case.

In the example of FIG. 21, the laser light L1 is applied to the wavelength converter 4 after being reflected from the optical filter 7. The inner surface 55*b* of the recess 55 on the substrate is, for example, truncated conical with the side surface and the upper surface. The opening 55*a* of the recess 55 is, for example, circular. The wavelength converter 4 is located at, for example, the bottom of the inner surface 55*b* of the recess 55 (specifically, on the surface corresponding to the upper surface of the truncated cone). The hole 56 in the substrate 5 extends, for example, upward from below while being inclined in the negative X-direction. The hole 56 is open, for example, on the side surface of the inner surface 55*b* of the recess 55. The laser light L1 travels through the opening 56*a* of the hole 56 and the opening 55*a* of the recess 55 directly to the optical filter 7. The optical filter 7 reflects the laser light L1 toward the wavelength converter 4. The wavelength converter 4 may be located, on the inner surface 55*b* of the recess 55, in an area other than in the example of FIG. 11.

Figure 22:
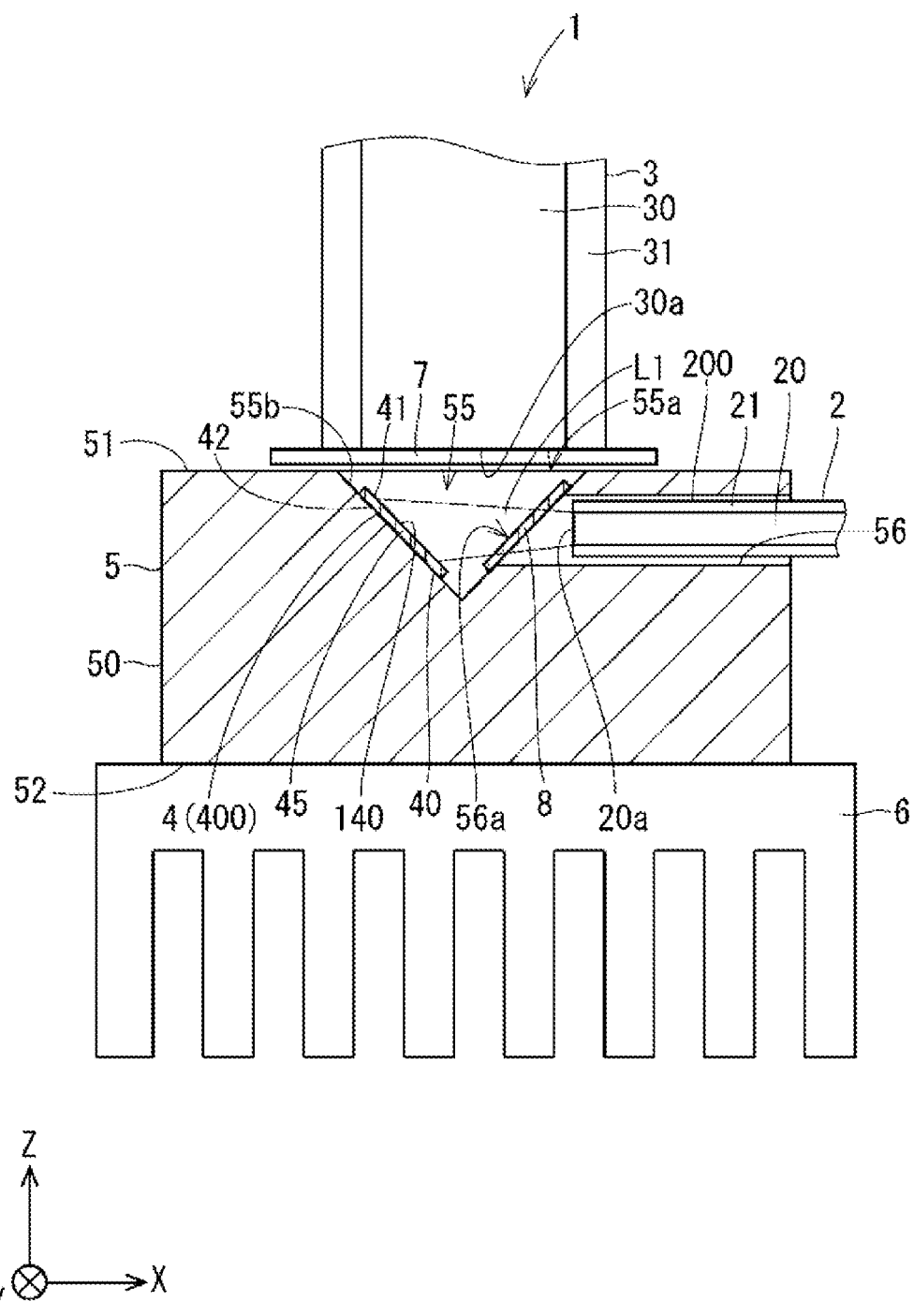
FIG. 22 is a schematic diagram of an example optical connector.
Figure 23:
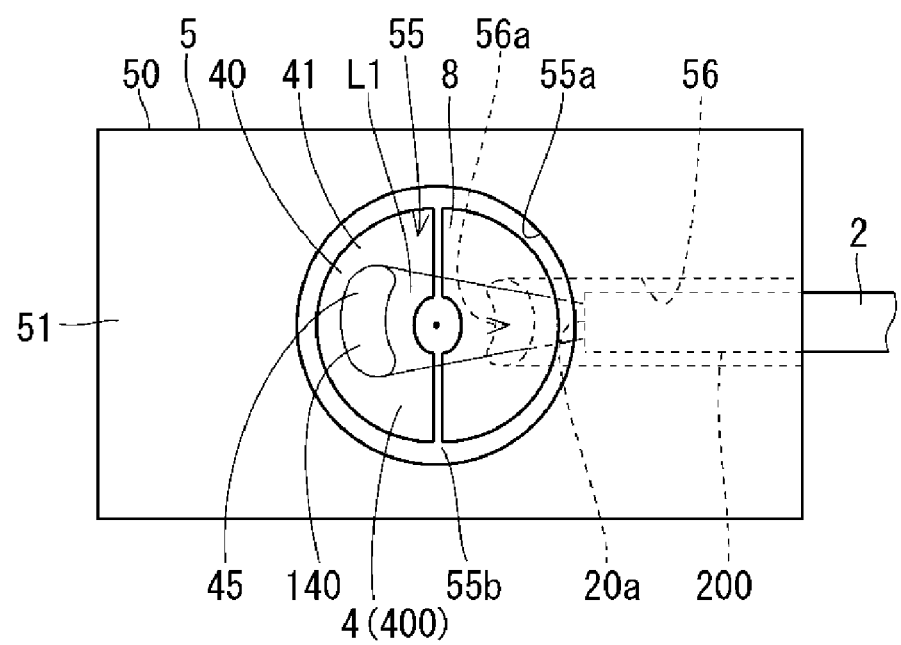
FIG. 23 is a schematic diagram of an example optical connector.

The optical connector 1 may include an optical filter 8 (also referred to as a second optical filter) that covers at least a portion of the opening 56*a* of the hole 56. The optical filter 8 reflects the conversion light L2 and transmits the laser light L1. FIG. 22 is a schematic diagram of an example optical connector 1 including the optical filter 8. FIG. 23 is a schematic diagram of examples of the wavelength converter 4, the substrate 5, and the optical fiber 2 illustrated in FIG. 22 as viewed in the positive Z-direction. In FIG. 22, the cross section of the optical filter 8 is hatched with diagonal lines.

In the example of FIGS. 22 and 23, the optical filter 8 covers, for example, the entire area of the opening 56*a* of the hole 56. The optical filter 8 is, for example, a plate, a sheet, or a film. The optical filter 8 is located on the inner surface 55*b* of the recess 55 to cover, for example, most of the half (in the positive X-direction) with the opening 56*a* of the hole 56. The optical filter 8 is curved in conformance with the shape of the inner surface 55*b* of the recess 55. The optical filter 8 may have a thickness of, for example, 0.05 to 0.2 mm inclusive. The laser light L1 is applied directly to the wavelength converter 4 through the optical filter 8.

The optical filter 8 may have a reflectance for the conversion light L2 of, for example, not less than 80, 90, or 95%. The optical filter 7 may have a transmittance for the laser light L1 of, for example, not less than 80, 90, or 95%. The optical filter 8 may be made of, for example, glass or a material other than glass.

The optical filter 8 covers the opening 56a of the hole 56 and reflects the conversion light L2. The optical filter 8 thus reflects the component, of the conversion light L2 emitted from the wavelength converter 4, directed to the opening 56a of the hole 56. The conversion light L2 includes the component reflected from the optical filter 8 to be incident on the input surface 30a of the optical fiber 3. This increases the intensity of the component of the conversion light L2 input into the optical fiber 3.

Figure 24:
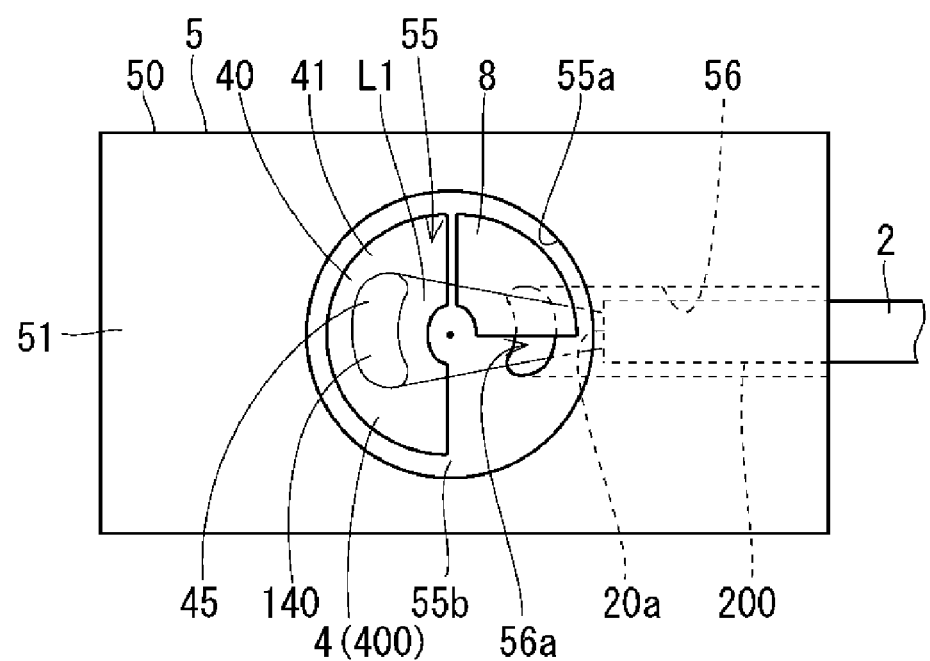
FIG. 24 is a schematic diagram of an example optical connector.
Figure 25:
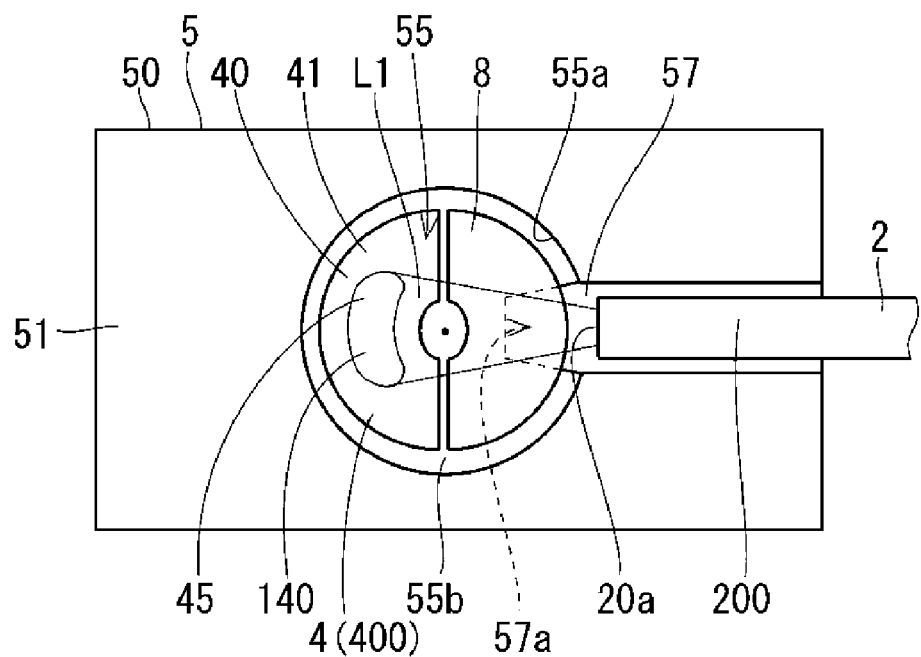
FIG. 25 is a schematic diagram of an example optical connector.

As in the example of FIG. 24, the optical filter 8 may partially cover the opening 56a of the hole 56. With the substrate 5 including the groove 57, as in the example of FIGS. 13 and 14, the optical filter 8 covering at least a portion of the opening 57a of the groove 57 may be included in the optical connector 1, as illustrated in FIG. 25.

Figure 26:
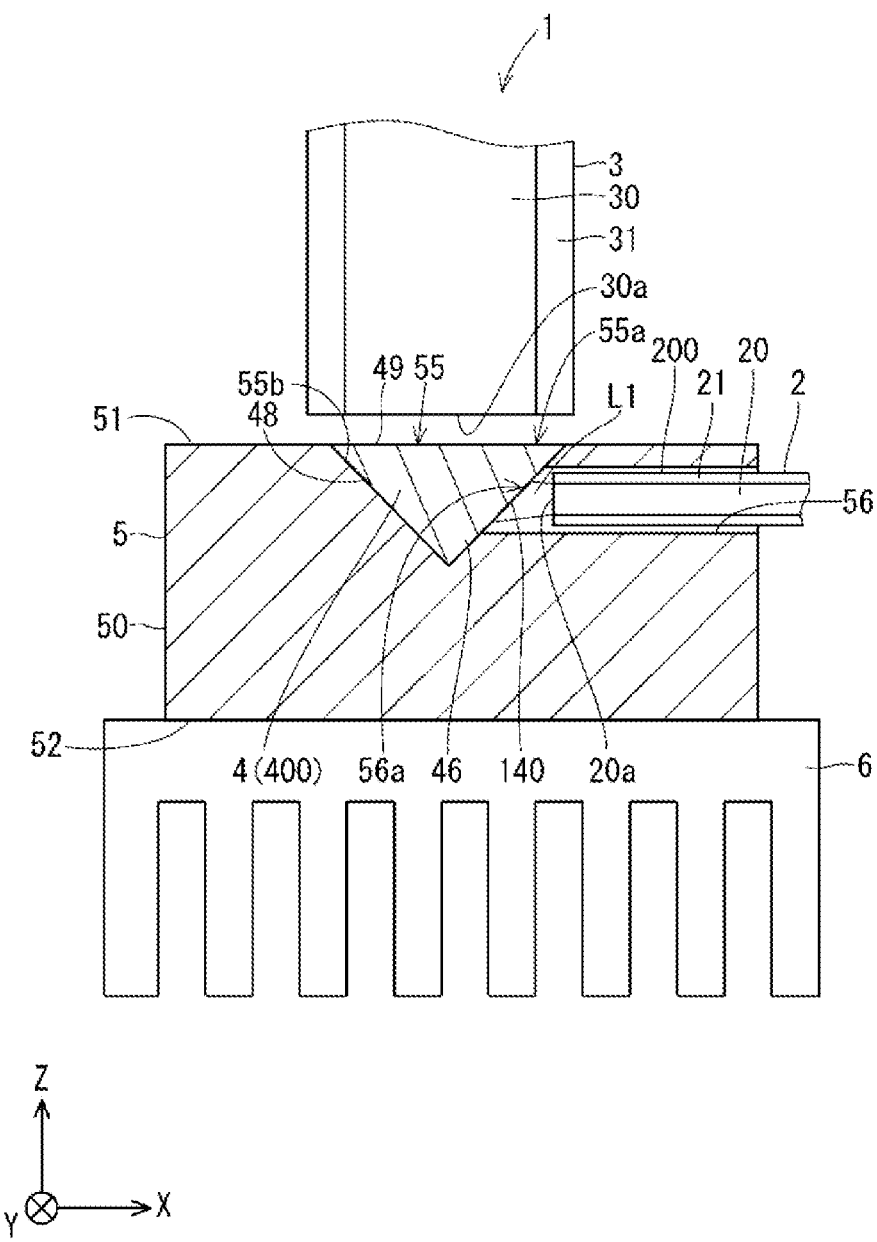
FIG. 26 is a schematic diagram of an example optical connector.

In each of the above examples, the wavelength converter 4 simply occupies a part of the space in the recess 55, but may be located in the recess 55 to fill the entire space in the recess as illustrated in FIG. 26. In the example of FIG. 26, the wavelength converter 4 is, for example, conical. The wavelength converter 4 includes a conical peripheral side surface 48 bonded to the inner surface 55b of the recess 55. The conversion light L2 emitted from the wavelength converter 4 includes the first component L2a emitted directly from the wavelength converter 4 through an upper surface 49 of the wavelength converter 4 (specifically, the surface corresponding to the bottom surface of the cone) and input directly into the optical fiber 3. The conversion light L2 further includes the second component L2b emitted through the peripheral side surface 48 of the wavelength converter 4, reflected from the substrate 5, and then input into the optical fiber 3. In the example of FIG. 26, the wavelength converter 4 includes the peripheral portion 46 located on the periphery of the opening 56a of the hole 56.

In the example of FIG. 26, the upper surface 49 of the wavelength converter 4 is located on the same plane as the upper surface 51 of the substrate 5, but may be located above or below the upper surface 51.

Figure 27:
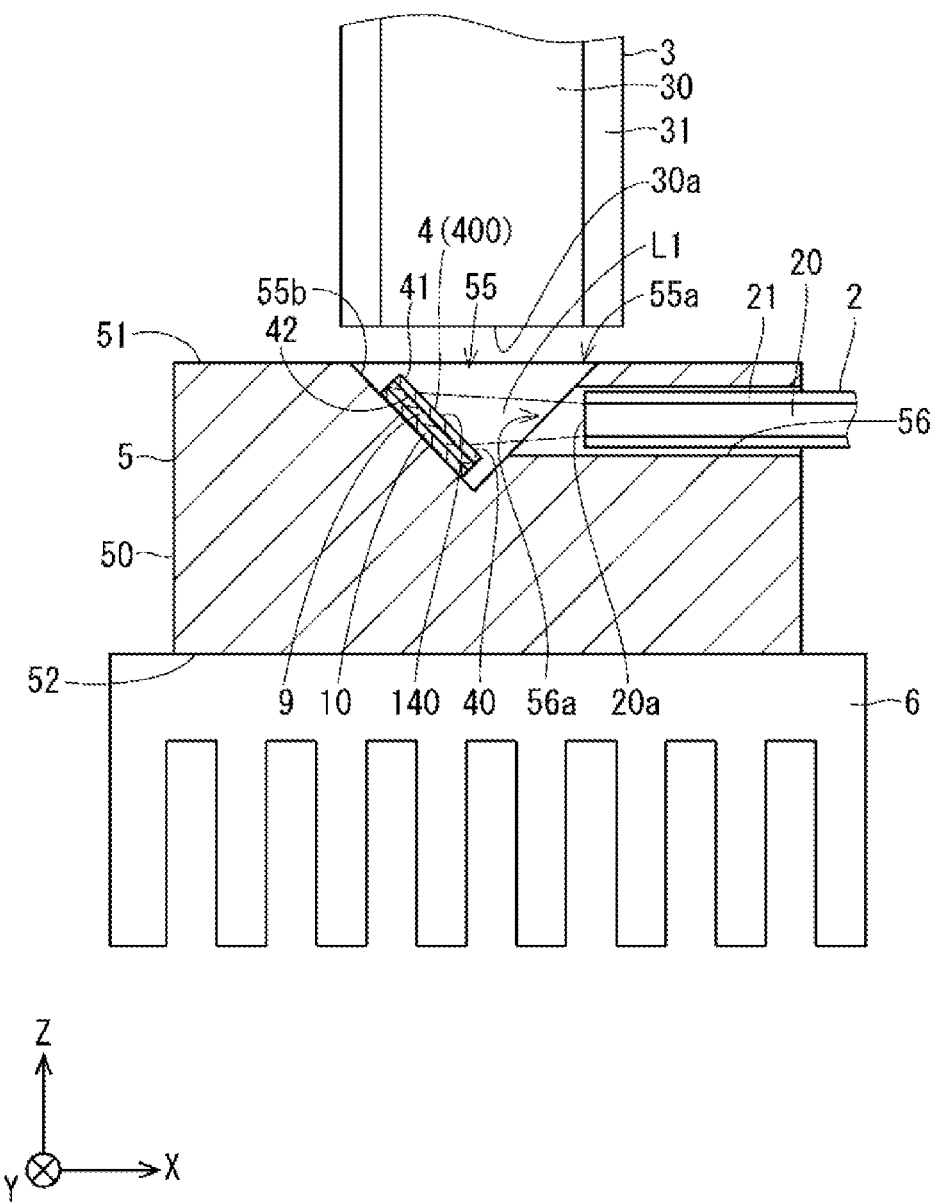
FIG. 27 is a schematic diagram of an example optical connector.

The wavelength converter 4 may be bonded to the substrate 5 with a method other than in the above examples. For example, the wavelength converter 4 may be bonded to the substrate 5 by placing the metal film 9 on the second surface 42 of the wavelength converter 4 and soldering the substrate 5 to the metal film 9. FIG. 27 is a schematic diagram of an example optical connector 1 in this case. In FIG. 27, the cross sections of the metal film 9 and the solder layer 10 are hatched with diagonal lines. In this example, the solder layer 10 between the metal film 9 and the substrate solders the metal film 9 to the inner surface 55b of the recess 55 on the substrate 5.

Figure 28:
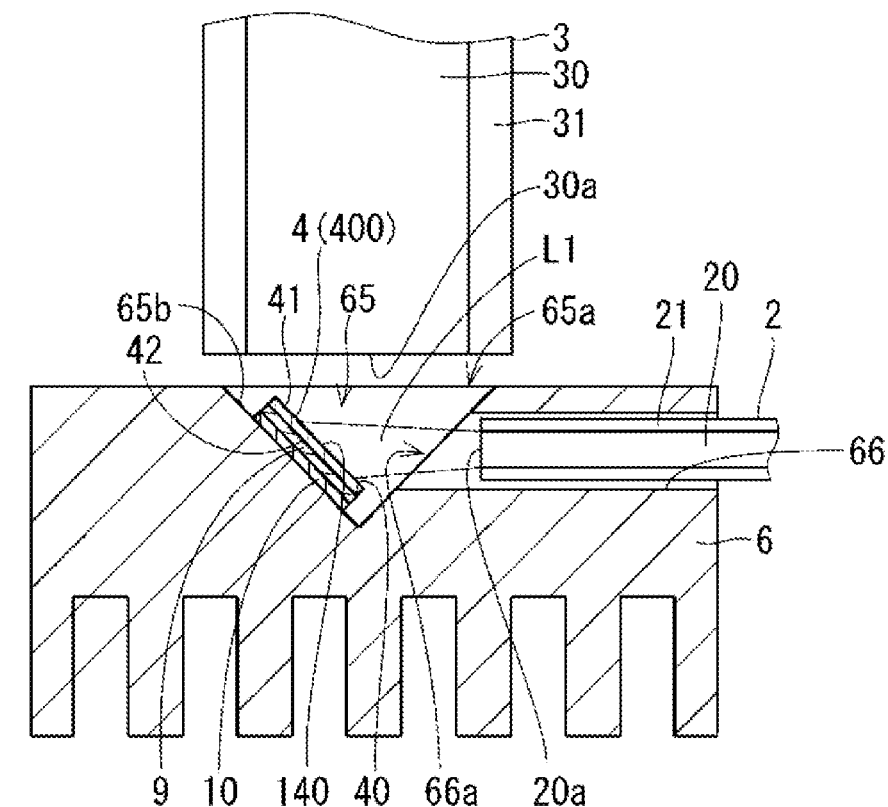
FIG. 28 is a schematic diagram of an example optical connector.

As illustrated in FIG. 28, the optical connector 1 may not include the substrate 5. In the example of FIG. 28, the metal film 9 on the second surface 42 of the wavelength converter 4 is soldered to the heat dissipater 6. The solder layer 10 is located between the metal film 9 and the heat dissipater 6. The heat dissipater 6 includes a recess 65. The recess 65 includes an opening 65a that is open on the upper surface of the heat dissipater 6. The wavelength converter 4 and the metal film 9 are located in the recess 65. The metal film 9 is soldered to an inner surface 65b of the recess 65. The heat dissipater 6 includes a hole 66 in which at least the output end 200 of the optical fiber 2 is embedded. The hole 66 includes an opening 66a connecting with a space in the recess 65. The laser light L1 is applied directly to the wavelength converter 4 through the opening 66a. The conversion light L2 includes a component that is input into the optical fiber 3 through the opening of the recess 65.

Figure 29:
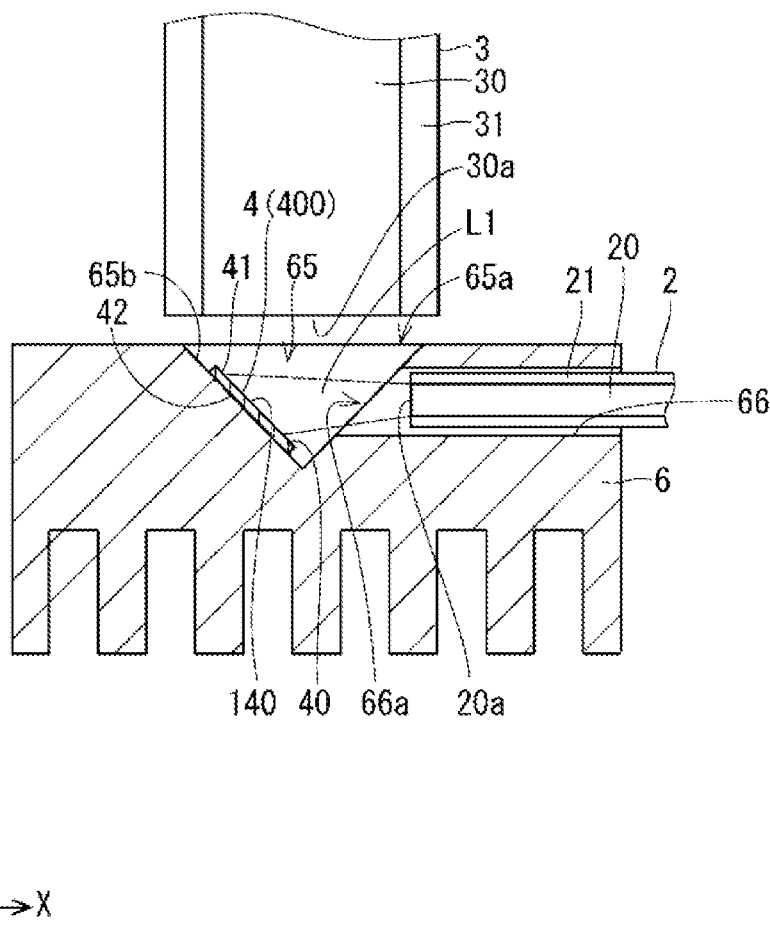
FIG. 29 is a schematic diagram of an example optical connector.

For the optical connector 1 not including the substrate 5, the wavelength converter 4 may be bonded directly to the heat dissipater 6 using no bonding material such as solder, as illustrated in FIG. 29. In the example of FIG. 29, the second surface 42 of the wavelength converter 4 is bonded directly to the inner surface 65b of the recess 65 of the heat dissipater 6. For example, the wavelength converter 4 may be bonded directly to the heat dissipater 6 by oxygen bonding in the same or similar manner as with the bonding of the wavelength converter 4 to the substrate 5. In another example, the wavelength converter 4 may be bonded directly to the heat dissipater 6 with, for example, minute recesses and protrusions of a few micrometers on the surface of the heat dissipater 6 that anchor the wavelength converter 4.

In this example as well, the reflectance of the high-reflectance member for the conversion light L2 may not be greater across the entire surface of the high-reflectance member than the reflectance of the surface 40 of the wavelength converter 4 for the conversion light L2. For example, the area of the surface of the high-reflectance member with a greater reflectance for the conversion light L2 than on the surface 40 of the wavelength converter 4 may be the inner surface of the recess alone in which the wavelength converter 4 is located. The reflectance of the high-reflectance member for the laser light L1 may not be greater than the reflectance of the surface 40 of the wavelength converter 4 for the laser light L1 across the entire surface of the high-reflectance member. For example, the area of the surface of the high-reflectance member with a greater reflectance for the laser light L1 than on the surface 40 of the wavelength converter 4 may be the inner surface of the recess alone in which the wavelength converter 4 is located. When, for example, the substrate 5 functions as a high-reflectance member as in the examples of FIG. 1 and other figures, and is made of an aluminum alloy or aluminum, the areas of the surface 50 of the substrate 5 other than the inner surface 55b of the recess 55 may have a black anodized finish to enhance the heat dissipation of the substrate 5. This causes the inner surface 55b of the recess 55 alone in the surface 50 of the substrate 5 to have a greater reflectance for the conversion light L2 than on the surface 40 of the wavelength converter 4. This also causes the inner surface 55b of the recess 55 alone in the surface 50 of the substrate 5 to have a greater reflectance for the laser light L1 than on the surface 40 of the wavelength converter 4. The same or similar finish may be applied to the metal film 9 that functions as a high-reflectance member. The same or similar finish may be applied to the heat dissipater 6 that functions as a high-reflectance member.

Figure 30:
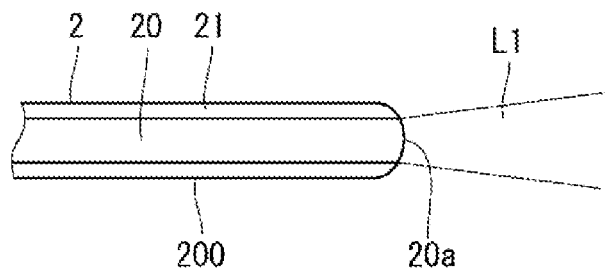
FIG. 30 is a schematic diagram of an example optical fiber.

In the above examples, the output surface 20a of the optical fiber 2 is a flat surface, but may be a convex surface, as illustrated in FIG. 30. In other words, the output surface 20a may be curved outward. In the example of FIG. 30, the overall end face on the output end of the optical fiber 2 is convex. The output surface 20a being convex functions as a convex lens. This allows the shape of the spot (e.g., the spot diameter) in the illumination area 140 of the laser light L1 to be easily adjusted by changing the shape of the convex surface as the output surface 20a.

Figure 31:
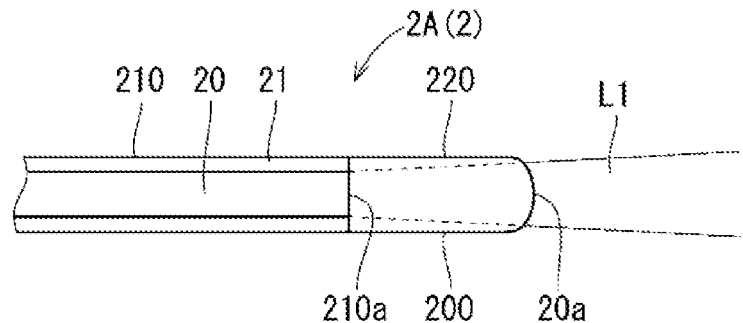
FIG. 31 is a schematic diagram of an example optical fiber.

With the convex output surface 20a of the optical fiber 2, the optical fiber 2 may include a coreless fiber as the output end 200. FIG. 31 is a schematic diagram of an example optical fiber 2 in this case.

The optical fiber 2 (also referred to as an optical fiber 2A) illustrated in FIG. 31 includes a fiber 210 (also referred to as an optical fiber 210 or a fiber body 210) with the core 20 and the cladding 21 described above, and a coreless fiber 220 connected to an end face 210a on the output end of the fiber 210.

The laser light L1 is input into the fiber 210, which transmits the input laser light L1. The end face 210a on the output end of the fiber 210 is, for example, flat. The coreless fiber 220 is connected to, for example, the end face on the output end of the core 20 and the end face on the output end of the cladding 21. The coreless fiber 220 is connected to the end face 210a on the output end of the fiber 210 by, for example, fusion splicing.

The laser light L1 to be transmitted by the fiber 210 is input into the coreless fiber 220. The coreless fiber 220 transmits the input laser light L1 and outputs the laser light L1 through the distal end. The end face on the output end of the coreless fiber 220 is a convex surface that serves as the output surface 20a of the optical fiber 2. The coreless fiber 220 is, for example, made of a material with a refractive index equal to or close to the refractive index of the core 20 for the laser light L1. The coreless fiber 220 may be made of the same material as the core 20 or of a different material from the core 20. For the core 20 made of, for example, quartz glass, the coreless fiber 220 may be made of, for example, quartz glass. In the coreless fiber 220, the laser light L1 expands while propagating. The laser light L1 is then output through the output surface 20a at the distal end of the coreless fiber 220.

The optical connector 1 as described above can be used in various systems. An example configuration of a system including the optical connector 1 will now be described.

Figure 32:
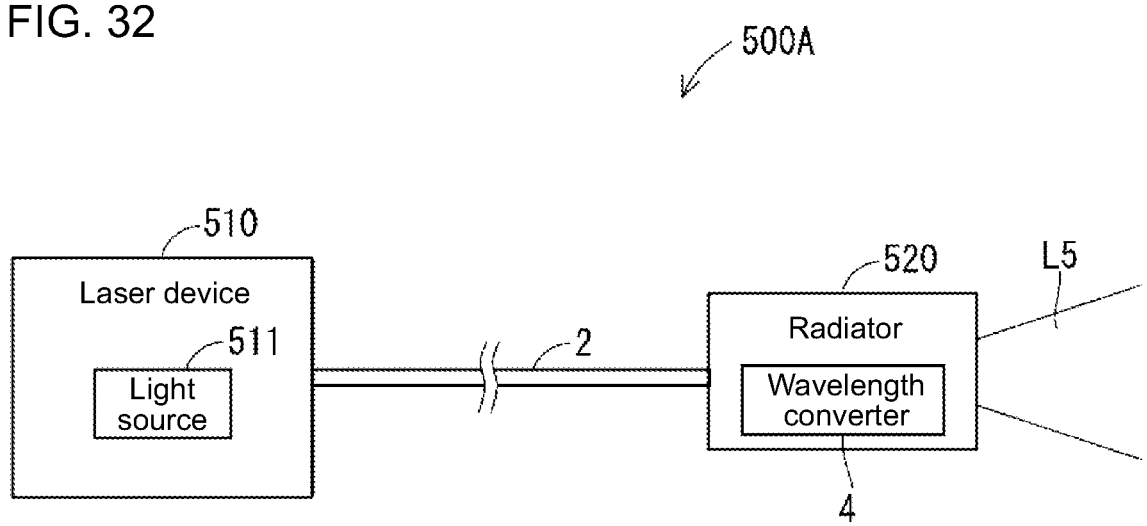
FIG. 32 is a schematic diagram of an example system including any of the optical connectors.

FIG. 32 is a schematic diagram of an example system 500A including any of the above optical connectors 1. The system 500A illustrated in FIG. 32 is, for example, an illumination system that radiates the conversion light L2 emitted from the wavelength converter 4 in the optical connector 1 as illumination light L5. The illumination light L5 radiated by the system 500A may be used indoors or outdoors.

As illustrated in FIG. 32, the system 500A includes, for example, a laser device 510, a radiator 520 that radiates the illumination light L5, and the optical fiber 2 described above. The radiator 520 includes the components of the optical connector 1 other than the optical fiber 2. The laser device 510 is connected to the radiator 520 with the optical fiber 2.

The laser device 510 can generate the laser light L1 and input it into the optical fiber 2. The laser device 510 includes a light source 511. The light source 511 generates and outputs the laser light L1. The light source 511 is, for example, a laser diode (LD). A laser diode is also referred to as a semiconductor laser. The laser light L1 output from the light source 511 is input into the optical fiber 2.

The output power of the laser light L1 of the laser device 510 is, for example, from several watts (W) to 10 W inclusive. The output power of the laser light L1 is not limited to this example. When the laser device 510 includes multiple light sources 511, the output power of the laser light L1 of the laser device 510 may be, for example, not less than 10 W.

The optical fiber 2 transmits the laser light L1 output from the light source 511 to the radiator 520. The optical fiber 2 transmits the laser light L1 output from the light source 511 and outputs the laser light L1 through the output surface 20a. The optical fiber 2 includes one end connected to the laser device 510, and the other end connected to the radiator 520. The optical fiber 2 may be connected to the laser device 510 with a connector or may be connected with another method.

The optical fiber 2 may be connected to the radiator 520 with a connector or may be connected with another method.

The optical fiber 2 extends into the radiator 520. The output surface 20a of the optical fiber 2 is located near the wavelength converter 4 in the radiator 520, as illustrated in FIG. 1 and other figures. The laser light L1 output through the output surface 20a of the optical fiber 2 is applied to the wavelength converter 4 in the radiator 520. The radiator 520 includes, for example, an optical fiber 3 with a short length. The conversion light L2 emitted from the wavelength converter 4 in the radiator 520 is input into the optical fiber 3 in the radiator 520. The optical fiber 3 transmits the conversion light L2 incident on its input surface 30a within the radiator 520. The conversion light L2 output from the optical fiber 3 is radiated outside the radiator 520 as the illumination light L5. The radiator 520 may include an optical system that receives input conversion light L2 output from the optical fiber 3. The optical system may include at least one of a lens, a diffuser, or a reflector. When the radiator 520 includes an optical system, the radiator 520 may adjust the light distribution of the illumination light L5. In the radiator 520, for example, a rod lens may be used as the light receiver 3 instead of the optical fiber 3. The light receiver 3 may also be, for example, an integrator lens, a hollow mirror, or a light guide.

Figure 33:
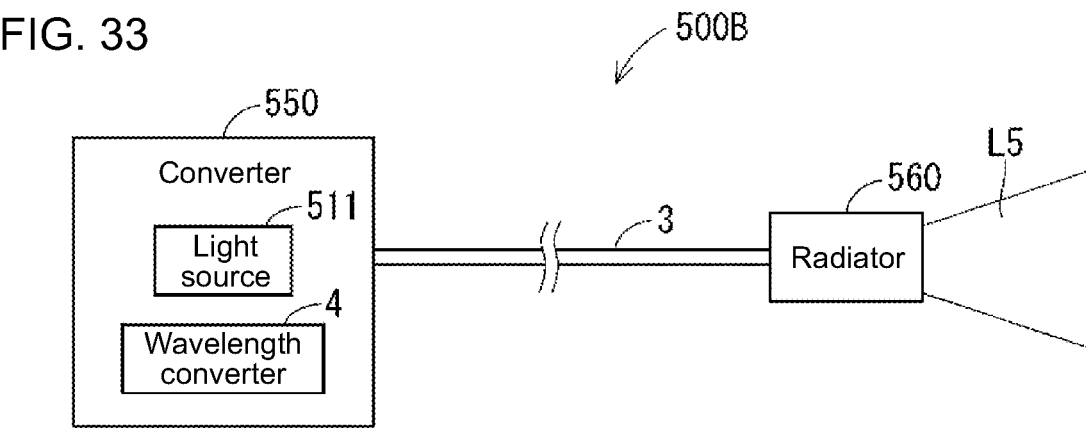
FIG. 33 is a schematic diagram of an example system including any of the optical connectors.

FIG. 33 is a schematic diagram of another example system 500B including any of the above optical connectors 1. The system 500B is, similarly to the system 500A, an illumination system that radiates the conversion light L2 emitted from the wavelength converter 4 in the optical connector 1 as the illumination light L5.

As illustrated in FIG. 33, the system 500B includes, for example, a converter 550 that generates the laser light L1 and converts the generated laser light L1 to the light L2, a radiator 560 that radiates the illumination light L5, and the optical fiber 3 described above. The converter 550 includes the components of the optical connector 1 other than the optical fiber 3. The converter 550 is connected to the radiator 560 with the optical fiber 3. The optical fiber 3 includes one end connected to the converter 550, and the other end connected to the radiator 560. The optical fiber 3 may be connected to the converter 550 with a connector or may be connected with another method. The optical fiber 3 may be connected to the radiator 560 with a connector or may be connected with another method.

The converter 550 includes the light source 511. The converter 550 includes, for example, an optical fiber 2 with a short length. The laser light L1 output from the light source 511 is input into the optical fiber 2 in the converter 550. The optical fiber 2 transmits the received laser light L1 within the converter 550 and outputs the laser light L1 through the output surface 20a. The laser light L1 emitted from the optical fiber 2 is applied to the wavelength converter 4 in the converter 550. The converter 550 may include, for example, a rod lens as the light emitter 2 instead of the optical fiber 2. The light emitter 2 may also be, for example, an integrator lens, a hollow mirror, or a light guide.

The optical fiber 3 extends into the converter 550. The input surface 30a of the optical fiber 3 is located near the wavelength converter 4 in the converter 550, as illustrated in FIG. 1 and other figures. The conversion light L2 emitted from the wavelength converter 4 is input into the input surface 30a of the optical fiber 3. The optical fiber 3 transmits the received conversion light L2 to the radiator 560.

The radiator 560 radiates the conversion light L2 output from the optical fiber 3 outside as the illumination light L5.

The radiator 560 may include an optical system into which the conversion light L2 is input. The optical system may include at least one of a lens, a diffuser, or a reflector. For the radiator 560 including an optical system, the radiator 560 may adjust the light distribution of the illumination light L5.

Figure 34:
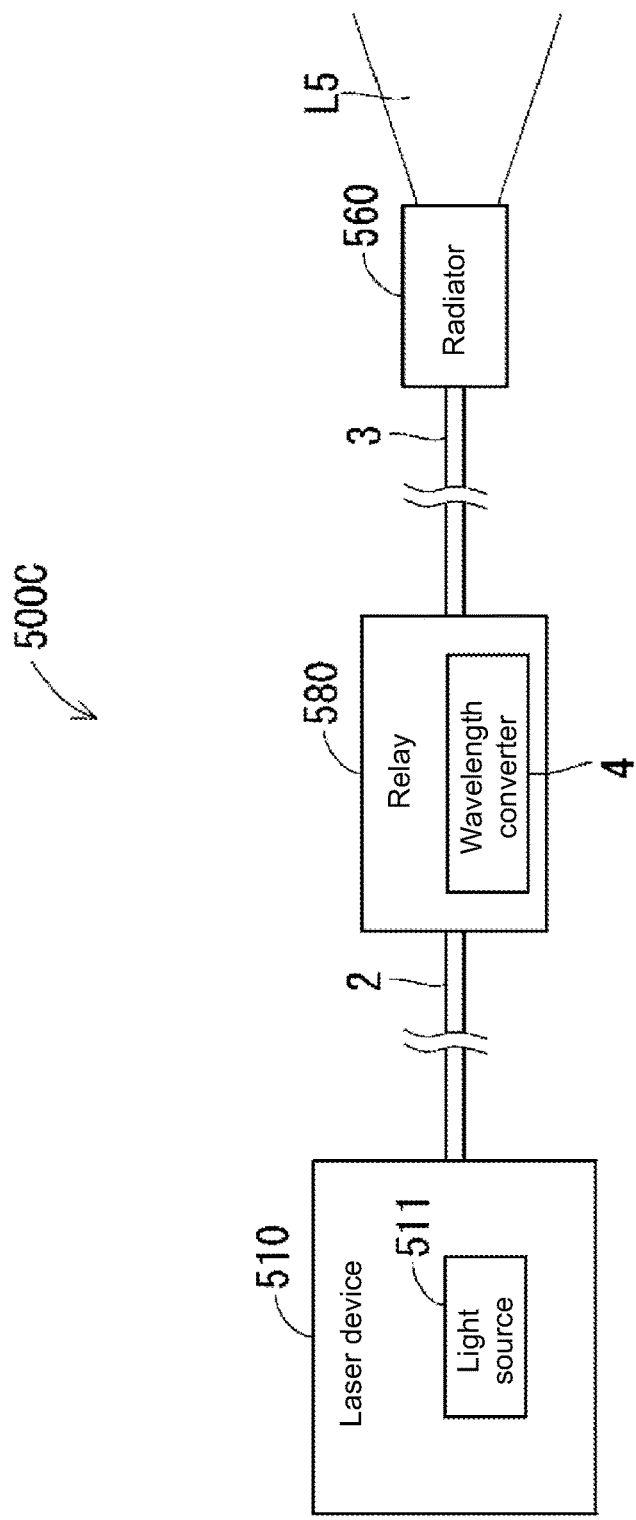
FIG. 34 is a schematic diagram of an example system including any of the optical connectors.

FIG. 34 is a schematic diagram of another example system 500C including any of the above optical connectors 1. The system 500C is, similarly to the systems 500A and 500B, an illumination system that radiates the conversion light L2 emitted from the wavelength converter 4 in the optical connector 1 as the illumination light L5.

As illustrated in FIG. 34, the system 500C includes, for example, the laser device 510 and the radiator 560 described above, a relay 580, and the optical fibers 2 and 3. The relay 580 includes the components of the optical connector 1 other than the optical fibers 2 and 3.

The laser device 510 is connected to the relay 580 with the optical fiber 2. The optical fiber 2 includes one end connected to the laser device 510, and the other end connected to the relay 580. The optical fiber 2 may be connected to the laser device 510 with a connector or may be connected with another method. The optical fiber 2 may be connected to the relay 580 with a connector or may be connected with another method.

The relay 580 is connected to the radiator 560 with the optical fiber 3. The optical fiber 3 includes one end connected to the relay 580, and the other end connected to the radiator 560. The optical fiber 3 may be connected to the relay 580 with a connector or may be connected with another method. The optical fiber 3 may be connected to the radiator 560 with a connector or may be connected with another method.

The optical fiber 2 transmits the laser light L1 output from the light source 511 in the laser device 510 to the relay 580. The optical fiber 2 extends into the relay 580. The output surface of the optical fiber 2 is located near the wavelength converter 4 in the relay 580, as illustrated in FIG. 1 and other figures. The laser light L1 output through the output surface 20a of the optical fiber 2 is applied to the wavelength converter 4 in the relay 580.

The optical fiber 3 extends into the relay 580. The input surface 30a of the optical fiber 3 is located near the wavelength converter 4 in the relay 580, as illustrated in FIG. 1 and other figures. The conversion light L2 emitted from the wavelength converter 4 is input into the input surface 30a of the optical fiber 3. The optical fiber 3 transmits the received conversion light L2 to the radiator 560. The radiator 560 radiates the conversion light L2 output from the optical fiber 3 outside as the illumination light L5.

Systems including the optical connector 1 are not limited to the above examples. The optical connector 1 may be, for example, used in an endoscope system. In this case, the conversion light L2 emitted from the wavelength converter 4 is used as illumination light to illuminate the inside of a human body, such as the inside of the gastrointestinal tract. The optical connector 1 may also be used in systems other than illumination systems that radiate the illumination light L5. For example, the optical connector 1 may be used in a projector. In this case, the conversion light L2 emitted from the wavelength converter 4 may be used as the light source of the projector.

The optical connector and the systems including the optical connector have been described in detail as described above, but the foregoing structures are illustrative in all respects, and the disclosure is not limited to the above structures. All the features of the embodiments described above may be combined in use unless any contradiction arises. Many variations not specifically described above may be implemented without departing from the scope of the disclosure.

REFERENCE SIGNS 1 optical connector
2 light emitter (first optical fiber)
3 light receiver (second optical fiber)
4 wavelength converter
5 substrate
6 heat dissipater
7, 8 optical filter
9 metal film
30a input surface
41a first area
42 second surface
42a second area
51a third area
55 recess
55a, 56a, 57a opening
55b inner surface
56 hole
57 groove
200 output end
500A, 500B, 500C system (illumination system)
L1 laser light
L2 conversion light
L2a first component
L2b second component

The invention claimed is:

1. An optical connector, comprising:
a first optical fiber configured to emit laser light;
a wavelength converter configured to receive the laser light and emit light with a wavelength spectrum different from a wavelength spectrum of the laser light in response to the laser light;
a second optical fiber configured to receive input of the light; and
a member configured to reflect the light,
wherein the second optical fiber has a core diameter greater than a core diameter of the first optical fiber,
the wavelength converter includes a surface including
a first area to directly receive the laser light from the first optical fiber, and
a second area located on the member,
the member includes a surface including a third area, and
the member has a reflectance for the light in the third area greater than a reflectance of the wavelength converter for the light in the second area.

2. The optical connector according to claim 1, wherein
the third area receives a transmission component of the laser light transmittable through the wavelength converter, and
a reflectance for the laser light in the third area is greater than a reflectance of the wavelength converter for the laser light in the second area.

3. The optical connector according to claim 1, wherein
the second optical fiber for the light has a numerical aperture greater than a numerical aperture of the first optical fiber for the laser light.

4. The optical connector according to claim 1, wherein
the laser light in the first area has a spot diameter greater than a core diameter of the second optical fiber.

5. The optical connector according to claim 1, wherein
a distance between an input surface of a core in the second
   optical fiber and the wavelength converter is less than
   or equal to a core diameter of the second optical fiber.
6. The optical connector according to claim 1, wherein
the second optical fiber includes an input surface parallel
   to the first area.
7. The optical connector according to claim 1, wherein
the first optical fiber includes an output surface tilted from
   a direction parallel to the first area, the second optical
   fiber includes an input surface tilted from the direction
   parallel to the first area, and the output surface and the
   input surface are tilted in directions different from each
   other.

* * * * *